(12) United States Patent
Grobshtein et al.

(10) Patent No.: US 10,667,771 B2
(45) Date of Patent: Jun. 2, 2020

(54) NUCLEAR MEDICINE IMAGING SYSTEMS AND METHODS HAVING MULTIPLE DETECTOR ASSEMBLIES

(71) Applicant: General Electric Company, Schenectady, NY (US)

(72) Inventors: Yariv Grobshtein, Haifa (IL); Shai Wald, Haifa (IL); Gillan Michael Grimberg, Tel Aviv (IL); Ken Efrati, Kiryat Motzkin (IL); Jean-Paul Bouhnik, Zichron Yaacov (IL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/247,758

(22) Filed: Jan. 15, 2019

(65) Prior Publication Data

US 2019/0209108 A1     Jul. 11, 2019

Related U.S. Application Data

(63) Continuation of application No. 15/862,839, filed on Jan. 5, 2018, now Pat. No. 10,213,174.

(51) Int. Cl.
*G01T 1/166*     (2006.01)
*A61B 6/00*     (2006.01)
(Continued)

(52) U.S. Cl.
CPC ............ *A61B 6/4266* (2013.01); *A61B 6/037* (2013.01); *A61B 6/04* (2013.01); *A61B 6/4241* (2013.01);
(Continued)

(58) Field of Classification Search
CPC ....... A61B 6/4266; A61B 6/037; A61B 6/032; A61B 6/4275; G01T 1/1614;
(Continued)

(56) References Cited

U.S. PATENT DOCUMENTS

| | | | |
|---|---|---|---|
| 3,774,031 A | 11/1973 | Mallard et al. | |
| 4,204,123 A | 5/1980 | Stoddart | |

(Continued)

FOREIGN PATENT DOCUMENTS

| | | |
|---|---|---|
| EP | 2275989 A1 | 1/2011 |
| WO | 2008135994 A2 | 11/2008 |

(Continued)

OTHER PUBLICATIONS

International Search Report and Written Opinion for corresponding PCT Application No. PCT/IL2014/050848 dated Feb. 5, 2015 (10 pages).

(Continued)

*Primary Examiner* — Kiho Kim
(74) *Attorney, Agent, or Firm* — The Small Patent Law Group LLC; Dean D. Small

(57) ABSTRACT

Nuclear medicine (NM) imaging system includes a plurality of detector assemblies that each have a movable arm and a detector head that is coupled to the movable arm. The movable arm is configured to move the detector head toward and away from an object. The NM imaging system also includes at least one processor configured to determine a body contour of the object and determine an acquisition configuration using the body contour. The acquisition configuration includes at least three of the detector heads positioned in a dense group that borders the body contour. The detector heads in the dense group are primary detector heads. The at least one processor is also configured to move at least one of the object or one or more of the primary detector heads so that the primary detector heads are in the dense group near the object.

20 Claims, 19 Drawing Sheets

(51) Int. Cl.
  *G01T 1/161* (2006.01)
  *G01T 1/29* (2006.01)
  *A61B 6/03* (2006.01)
  *G01T 1/16* (2006.01)
  *A61B 6/04* (2006.01)
  G01T 1/163 (2006.01)
  G01B 11/24 (2006.01)
  G01T 1/164 (2006.01)

(52) U.S. Cl.
  CPC .......... *G01T 1/1603* (2013.01); *G01T 1/1614* (2013.01); *G01T 1/2985* (2013.01); *A61B 6/032* (2013.01); *A61B 6/4275* (2013.01); *A61B 6/5205* (2013.01); *G01B 11/2433* (2013.01); *G01T 1/1635* (2013.01); *G01T 1/1642* (2013.01)

(58) Field of Classification Search
  CPC ... G01T 1/1635; G01T 1/2985; G01T 1/1648; G01T 1/1642; G01B 11/2433
  See application file for complete search history.

(56) References Cited

U.S. PATENT DOCUMENTS

| | | | |
|---|---|---|---|
| 5,047,641 A | 10/1991 | Besseling et al. | |
| 5,252,830 A | 10/1993 | Weinberg | |
| 5,376,796 A * | 12/1994 | Chan | G01B 11/2433 250/363.02 |
| 5,436,958 A | 7/1995 | Taylor | |
| 5,552,606 A * | 9/1996 | Jones | G01T 1/1611 250/363.04 |
| 5,594,251 A | 1/1997 | Fleury et al. | |
| 5,675,513 A | 10/1997 | Hammer | |
| 5,689,543 A | 11/1997 | Graves et al. | |
| 5,717,212 A | 2/1998 | Fulton et al. | |
| 5,949,842 A | 9/1999 | Schafer et al. | |
| 6,114,701 A | 9/2000 | Plummer et al. | |
| 6,140,650 A | 10/2000 | Berlad | |
| 6,147,353 A | 11/2000 | Gagnon et al. | |
| 6,211,523 B1 * | 4/2001 | Gagnon | G01T 1/1648 250/363.02 |
| 6,239,438 B1 | 5/2001 | Schubert | |
| 6,256,404 B1 | 7/2001 | Gordon et al. | |
| 6,271,524 B1 | 8/2001 | Wainer et al. | |
| 6,279,420 B1 | 8/2001 | Knorowski et al. | |
| 6,388,244 B1 | 5/2002 | Gagnon | |
| 6,535,229 B1 | 3/2003 | Kraft | |
| 6,636,214 B1 | 10/2003 | Leather et al. | |
| 6,748,044 B2 | 7/2004 | Sabol et al. | |
| 6,943,355 B2 | 9/2005 | Shwartz et al. | |
| 7,026,623 B2 | 4/2006 | Oaknin et al. | |
| 7,223,240 B2 | 5/2007 | Murashita | |
| 7,280,638 B1 | 10/2007 | Weaver et al. | |
| 7,381,959 B2 | 6/2008 | Manjeshwar et al. | |
| 7,447,343 B2 | 11/2008 | Barfuss et al. | |
| 7,555,164 B2 | 6/2009 | Lin | |
| 7,601,966 B2 | 10/2009 | Ben-Haim et al. | |
| 7,671,331 B2 | 3/2010 | Hefetz | |
| 7,705,316 B2 | 4/2010 | Rousso et al. | |
| 7,755,057 B2 | 7/2010 | Kim | |
| 7,829,856 B2 | 11/2010 | Jansen et al. | |
| 7,907,990 B2 | 3/2011 | Ferenczi et al. | |
| 8,194,237 B2 | 6/2012 | Cronin et al. | |
| 8,280,124 B2 | 10/2012 | Dichterman et al. | |
| 8,338,788 B2 | 12/2012 | Zilberstein et al. | |
| 8,421,021 B2 | 4/2013 | Sachs et al. | |
| 8,455,834 B2 | 6/2013 | Tsukerman | |
| 8,479,213 B2 | 7/2013 | Jones et al. | |
| 8,487,265 B2 | 7/2013 | Heukensfeldt Jansen et al. | |
| 8,492,725 B2 | 7/2013 | Zilberstein et al. | |
| 8,542,892 B2 | 9/2013 | Kovalski | |
| 8,542,898 B2 | 9/2013 | Bathe et al. | |
| 8,610,075 B2 | 12/2013 | Rousso et al. | |
| 8,748,827 B2 | 6/2014 | Zilberstein et al. | |
| 8,757,555 B2 | 6/2014 | Werthmann et al. | |
| 8,841,619 B2 | 9/2014 | Volokh et al. | |
| 9,392,982 B2 | 7/2016 | Zingerman | |
| 9,402,595 B2 | 8/2016 | Steinfeld et al. | |
| 2002/0191828 A1 | 12/2002 | Colbeth et al. | |
| 2004/0223633 A1 | 11/2004 | Krishnan | |
| 2004/0262525 A1 | 12/2004 | Yunker et al. | |
| 2006/0108532 A1 * | 5/2006 | Ohana | G01T 1/1611 250/363.04 |
| 2007/0018108 A1 | 1/2007 | Kitamura | |
| 2007/0232881 A1 | 10/2007 | Shai et al. | |
| 2008/0001090 A1 | 1/2008 | Ben-Haim et al. | |
| 2008/0029704 A1 | 2/2008 | Hefetz et al. | |
| 2008/0092074 A1 | 4/2008 | Cohen | |
| 2008/0137806 A1 * | 6/2008 | Chang | A61B 6/032 378/17 |
| 2008/0145797 A1 | 6/2008 | Verbeke et al. | |
| 2009/0070121 A1 | 3/2009 | Leonelli et al. | |
| 2009/0168960 A1 | 7/2009 | Jongen et al. | |
| 2010/0001190 A1 | 1/2010 | Wjeczorek et al. | |
| 2010/0121604 A1 | 5/2010 | Vaisburd et al. | |
| 2011/0026685 A1 | 2/2011 | Zilberstein et al. | |
| 2011/0129061 A1 | 6/2011 | Janbakhsh | |
| 2012/0108948 A1 | 5/2012 | Jansen et al. | |
| 2012/0205542 A1 | 8/2012 | Goedicke et al. | |
| 2012/0248320 A1 * | 10/2012 | Wangerin | G01T 1/166 250/363.05 |
| 2013/0120200 A1 | 5/2013 | Desclos et al. | |
| 2013/0123602 A1 | 5/2013 | Kovalski et al. | |
| 2013/0168567 A1 | 7/2013 | Wartski et al. | |
| 2013/0308749 A1 * | 11/2013 | Zilberstein | G01T 1/1611 378/19 |
| 2013/0320234 A1 | 12/2013 | Volokh et al. | |
| 2014/0126793 A1 | 5/2014 | Ahn et al. | |
| 2014/0343412 A1 | 11/2014 | Wjecxorek et al. | |
| 2015/0065873 A1 | 3/2015 | Tsukerman et al. | |
| 2015/0065874 A1 | 3/2015 | Rafaeli et al. | |
| 2015/0119704 A1 | 4/2015 | Roth et al. | |
| 2015/0208999 A1 * | 7/2015 | Steinfeld | G01T 1/16 378/205 |
| 2015/0327831 A1 | 11/2015 | Levin et al. | |
| 2017/0014096 A1 | 1/2017 | Bouhnik et al. | |

FOREIGN PATENT DOCUMENTS

| | | |
|---|---|---|
| WO | 2009036078 A2 | 3/2009 |
| WO | 2014165472 A1 | 10/2014 |

OTHER PUBLICATIONS

Meikle et al. "Accelerated EM Reconstruction in Total-Body PET: Potential for Improving Tumour Detectability" Physics in Medicine and Biology; vol. 39, Issue 10; 1994 (16 pages).

Park et al. "Performance of a High-Sensitivity Dedicated Cardiac SPECT Scanner for Striatal Uptake Quantification in the Brain Based on Analysis of Projection Data" Medical Physics 40; No. 4; 2013 (8 pages).

Riddell et al. "Noise Reduction in Oncology FDG PET Images by Iterative Reconstruction: A Quantitative Assessment" The Journal of Nuclear Medicine; vol. 42, No. 9; 2001 ( 8 pages).

Shepp et al. "Maximum Likelihood Reconstruction for Emission Tomography" IEEE Transactions on Medical Imaging; vol. MI-1, No. 2; 1982 (10 pages).

* cited by examiner

NUCLEAR MEDICINE IMAGING SYSTEMS AND METHODS HAVING MULTIPLE DETECTOR ASSEMBLIES

CROSS-REFERENCE TO RELATED APPLICATIONS

The present application is a continuation of U.S. patent application Ser. No. 15/862,839, filed on Jan. 5, 2018, which is incorporated herein by reference in its entirety.

BACKGROUND

The subject matter disclosed herein relates generally to multi-head nuclear medicine (NM) imaging systems, and more particularly to multi-head NM imaging systems that are capable of selectively moving the detector heads relative to an object, such as a patient, within the multi-head NM imaging system.

In NM imaging, such as single photon emission computed tomography (SPECT) or positron emission tomography (PET) imaging, radiopharmaceuticals are administered internally to a patient. The radiopharmaceuticals emit radiation that may be captured by an NM imaging system to generate images for diagnostic review. An NM imaging system may be configured as a multi-head system having a number of individual detector assemblies. The detector assemblies may include a movable arm that is capable of moving radially-inward toward the patient and a detector head that is held by the movable arm. A positioning subsystem of the NM imaging system controls movement of the detector heads in order to position the detector heads and acquire images of a designated region-of-interest (ROI). For example, the detector heads may be positioned within a few centimeters from the patient to acquire images of the heart of the patient.

The patient is typically confined within a cavity (e.g., bore) of the NM imaging system during the imaging session while the detector heads are positioned relative to the patient. Prior to the imaging session in which the diagnostic images are obtained, the patient is positioned relative to the detectors so that a collective field-of-view of the NM imaging system includes the anatomical region of interest (e.g., heart, brain, etc.). At this time, one or more persistence images are obtained and reviewed to position the patient. The persistence images are typically only used to position the patient and, as such, have a lower quality than the images used for diagnosis. Persistence images may also be referred to as scout images. As the images are acquired, the technician reviews the images and incrementally moves the patient within the cavity of the gantry so that the anatomical region-of-interest is within the collective field-of-view. It is generally desirable to quickly position the patient, because the emissions from the radioisotopes reduce over time. During the time in which persistence images are acquired, a technician may also assess the activity of the radioisotopes for determining the scan duration. In a traditional single or dual head SPECT camera, when imaging the torso, such as in cardiac imaging, the patient is instructed to hold his hand above his head. This is done to allow the large detector heads to come closer to the torso as the detector heads rotate about the patient. To some patient this cause discomfort or may be impossible for patients with limited mobility.

The quality and reliability of the diagnostic images depends upon the number of emitted photons detected by the detector heads. As such, it is desirable to position the detector heads relative to the patient so that more photons may be detected. While the method described above can be effective, other methods that enable positioning the patient more quickly and/or acquiring photons at a greater rate are desired.

BRIEF DESCRIPTION

In one embodiment, a nuclear medicine (NM) imaging system is provided that includes a gantry including a cavity that is sized and shaped to receive an object therein. The cavity is oriented relative to mutually perpendicular longitudinal, vertical, and horizontal axes. The cavity extends lengthwise along the longitudinal axis. The NM imaging system also includes a plurality of detector assemblies distributed at least partially around the cavity. Each of the detector assemblies in the plurality includes a movable arm and a detector head that is coupled to the movable arm. The movable arm is configured to move the detector head toward and away from the object within the cavity. The NM imaging system also includes at least one processor configured to execute programmed instructions stored in memory. For example, the NM imaging system may have a control system that includes the at least one processor. The at least one processor, when executing the programmed instructions, is configured to determine a body contour of the object within the cavity. The body contour represents an exterior surface of the object positioned within the cavity. The at least one processor is also configured to determine an acquisition configuration using the body contour. The acquisition configuration includes at least three of the detector heads positioned in a dense group that borders the body contour. The detector heads in the dense group are primary detector heads. The at least one processor is also configured to move at least one of the object or one or more of the primary detector heads so that the primary detector heads are in the dense group near the object.

In some aspects, the dense group of the primary detector heads includes at least one of: (a) two or more of the primary detector heads being immediately adjacent to one another such that the primary detector heads abut each other or have a tolerance gap therebetween or (b) two or more of the primary detector heads being incapable of moving closer to the object because the primary detector heads are extended to a maximum length or blocked by another primary detector head.

In some aspects, the detector heads are spaced apart from adjacent detector heads by respective separation distances. The primary detector heads of the dense group have an average separation distance between one another. The average separation distance between the primary detector heads is less than an average separation distance between the other detector heads.

In some aspects, the longitudinal axis is a central longitudinal axis of the cavity and wherein each of the primary detector heads is positioned a working distance away from the longitudinal axis. The at least one processor is configured to determine imaging positions of the primary detector heads by calculating a minimum of an average of the working distances of the primary detector heads. The imaging positions are at least partially based on positions of the primary detector heads where the minimum occurs.

In some aspects, the detector heads are configured to move within a radial range defined between a minimum radial distance and a maximum radial distance. The maximum radial distance is a point at which the primary detector head cannot move closer to the object. The at least one processor is configured to determine imaging positions of the primary detector heads by calculating a maximum of an average of the radial distances of the primary detector heads. The imaging positions are at least partially based on positions of the primary detector heads where the maximum occurs.

In some aspects, the primary detector heads are separated from adjacent primary detector heads by separation distances. The at least one processor configured to determine imaging positions of the primary detector heads by calculating a minimum of an average of the separation distances. The imaging positions are at least partially based on positions of the primary detector heads where the minimum occurs.

In some aspects, the detector heads include photon detectors that are rotatable about a sweep axis. The at least one processor is configured to acquire persistence images by detecting photons at different rotational positions of the photon detectors. The at least one processor is also configured to determine imaging positions of the primary detector heads at which a maximum photon-detection rate is expected based on the persistence images.

In some aspects, the NM imaging system also includes a table positioned within the cavity and extending lengthwise along the longitudinal axis. The table is movable in a direction along the horizontal axis and movable in a direction along the vertical axis. The at least one processor is configured to request a local support for changing an orientation of the body contour with respect to the table, wherein the at least one processor moves the table and the at least one detector head based on the body contour supported by the local patient support.

In some aspects, the NM imaging system also includes a table positioned within the cavity and extending lengthwise along the longitudinal axis. The table is movable in a direction along the horizontal axis and movable in a direction along the vertical axis. The table is configured to position the patient for imaging a torso of the patient while at least one of the arms of the patient is supported along a local support that is outside the cavity.

In some aspects, the NM imaging system also includes an array of light emitters and an array of light detectors. Each of the light emitters is configured to direct light signals toward at least one of the light detectors, wherein the at least one processor is configured to determine the body contour based on the light detectors that do not detect the light signals from the light emitters when the object is positioned within the cavity.

In some aspects, the at least one processor is configured to determine the body contour using proximity sensor devices (PSDs) coupled to respective detector heads of the group of detector assemblies. The PSDs are activated when the PSDs engage the object or when the PSDs are within a predetermined distance from the object, wherein the detector assemblies communicate signals to the at least one processor. The signals are indicative of a position of the PSD.

In an embodiment, a method is provided that includes positioning an object within a cavity of a nuclear medicine (NM) imaging system. The NM imaging system includes a cavity that is sized and shaped to receive the object therein. The cavity is oriented relative to mutually perpendicular longitudinal, vertical, and horizontal axes. The cavity extends lengthwise along the longitudinal axis. The NM imaging system also includes a plurality of detector assemblies distributed at least partially around the cavity. Each of the detector assemblies in the plurality includes a movable arm and a detector head that is coupled to the movable arm. The method also includes determining a body contour of the object within the cavity. The body contour represents an exterior surface of the object positioned within the cavity. The method also includes determining an acquisition configuration using the body contour. The acquisition configuration includes at least three of the detector heads positioned in a dense group that borders the body contour. The detector heads in the dense group are primary detector heads. The method also includes moving at least one of the object or one or more of the primary detector heads so that the primary detector heads are in the dense group along the object.

In some aspects, the dense group of the primary detector heads includes at least one of: (a) two or more of the primary detector heads being immediately adjacent to one another such that the primary detector heads abut each other or have a tolerance gap therebetween; or (b) two or more of the primary detector heads being incapable of moving closer to the object because the primary detector heads are extended to a maximum radial distance or blocked by another primary detector head.

In some aspects, the detector heads are spaced apart from adjacent detector heads by respective separation distances. The primary detector heads of the dense group have an average separation distance between one another. The average separation distance between the primary detector heads is less than an average separation distance between the other detector heads.

In some aspects, the object is positioned on a table within the cavity. The method may also include positioning a local support between the table and the object, thereby changing an orientation of the body contour with respect to the table, and moving the body contour includes the body contour having the orientation changed by the local support.

In some aspects, the method may also include determining imaging positions of the primary detector heads, wherein the imaging positions of the primary detector heads are a function of at least one of: (i) a maximum of an average working distance of the primary detector heads from the longitudinal axis, the longitudinal axis being a central longitudinal axis of the cavity; (ii) a maximum of an average radial distance of the primary detector heads from respective starting positions; or (iii) a minimum of an average separation distance between the primary detector heads.

In some aspects, the detector heads include photon detectors that are rotatable about a sweep axis. The method also includes acquiring data for persistence images by detecting photons at different rotational positions of the photon detectors and determining the imaging positions of the primary detector heads at which a maximum photon-detection rate is expected.

In an embodiment, a method is provided that includes positioning a patient within a cavity of a nuclear medicine (NM) imaging system. The NM imaging system includes a cavity that is sized and shaped to receive the patient therein. The cavity is oriented relative to mutually perpendicular longitudinal, vertical, and horizontal axes. The cavity extends lengthwise along the longitudinal axis. The NM imaging system also includes a plurality of detector assemblies distributed at least partially around the cavity. Each of the detector assemblies in the plurality includes a movable arm and a detector head that is coupled to the movable arm. The method also includes determining a body contour of the patient within the cavity without an arm of the patient positioned alongside a torso of the patient. The body contour represents an exterior surface of the patient positioned within the cavity. The method also includes determining an acquisition configuration using the body contour. The acquisition configuration includes at least three of the detector heads positioned in a dense group that borders the body contour. The detector heads in the dense group are primary detector heads. The method also includes moving at least one of the patient or one or more of the primary detector heads so that the primary detector heads are in the dense group along the patient.

In some aspects, the method also includes providing a local support that is positioned proximate to the patient such that the arm of the patient may rest upon the local support during imaging.

In some aspects, the method also includes positioning a local support between the table and the patient, thereby changing an orientation of the body contour with respect to the table, wherein moving the table includes the body contour having the orientation changed by the local support.

DETAILED DESCRIPTION

Figure 1:
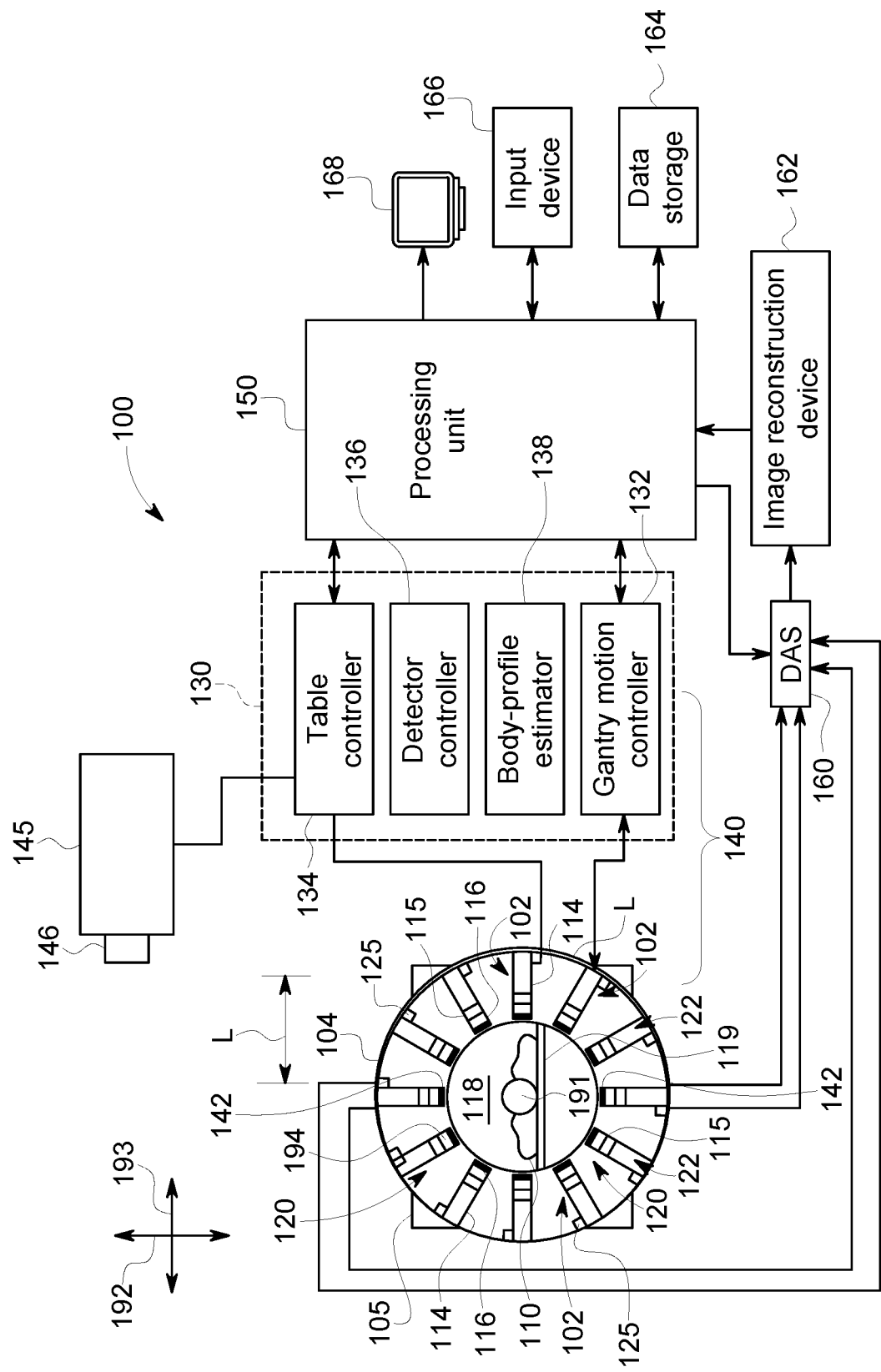
FIG. 1 provides a schematic view of a nuclear medicine (NM) imaging system in accordance with an embodiment.

Embodiments set forth herein include NM imaging systems and methods. The NM imaging system includes a plurality of detector heads that may be selectively positioned with respect to an object (e.g., patient). Particular embodiments may improve imaging settings by increasing a density of detector heads proximate to a region-of-interest (ROI). The detector heads are typically positioned closest to the ROI. To achieve a greater density, the object may be moved away (e.g., shifted vertically and/or laterally away) from the detector heads, thereby allowing the detector heads to extend further toward a center of the cavity. In such configurations, embodiments may be able to achieve shorter acquisition times, a reduced injection dose, and/or a decrease in patient discomfort. Patient discomfort especially occurs during long imaging sessions and can increase the likelihood that a patient will inadvertently move, thereby causing blurs in the image data.

The following description may use the term "patient" or the term "object" when referring to the subject that is imaged. Unless explicitly stated otherwise, it should be understood that either term may be replaced with the other in the claims. For example, although certain functions may be described below with respect to imaging a patient, it should be understood that the same functions may be used in imaging an object.

In some embodiments, a local support may be used to change the body contour of the patient. For example, a torso support may be positioned between the patient and the table. The torso support is designed to re-orient the patient (e.g., tilt the patient) thereby changing a position and/or orientation of the ROI. As another example, an arm support may be positioned outside of the NM imaging system. The patient may rest his or her arm on the arm support. As such, the arm is removed from the cavity, thereby allowing the detector heads to be positioned closer to the ROI. The other arm, which is away from the ROI (e.g., organ-of-interest, such as the heart), may stay within the cavity, optionally resting on the table, and optionally close or flush against the body. This prevents the detector head that is near the arm which is in the cavity to be close to the torso. However, only minor reduction of image quality may be caused as that detector head is away from the ROI and may contribute little to the image quality.

As used herein, the primary detector heads are positioned closer to the ROI and, as such, are able to detect more photons than other (secondary) detector heads. The primary detector heads may contribute more data for reconstructing the images. The primary detector heads are positioned closer to one another, thereby reducing any gaps that occur between the detector heads. With the gaps reduced in size, the image data may provide a more accurate and complete representation of the ROI.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be standalone programs, may be incorporated as subroutines in an operating system, may be functions in an installed software package, and the like. It should be understood that the various embodiments are not limited to the arrangements and instrumentality shown in the drawings.

As used herein, phrases such as "a plurality of [elements]" and the like, when used in the description and claims, do not necessarily refer to each and every element that a system may have. The system may have other elements that are similar to the plurality of elements but do not have the same features or limitations. For example, the phrase "a plurality of detector assemblies [being/having a recited feature or limitation]" does not necessarily mean that each and every detector assembly of the system has the recited feature or limitation. Other detector assemblies may not include the recited feature or limitation. Similarly, phrases such as "each of the detector assemblies [being/having a recited feature or limitation]" and the like, when used in the description and claims, does not preclude the possibility that the system may have other detector assemblies. Unless explicitly stated otherwise (e.g., "each and every detector assembly of the NM imaging system"), embodiments may include similar elements that do not have the recited features or limitations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Embodiments set forth herein include nuclear medicine (NM) imaging systems, methods of acquiring NM images, and computer readable media having one or more software modules that direct one or more processors to execute the methods described herein. Embodiments described herein and illustrated by the figures may be implemented in imaging systems, such as, for example, single photon emission computed tomography (SPECT), SPECT computed tomography (SPECT-CT), positron emission tomography (PET), PET-CT, SPECT magnetic resonance (SPECT-MR), and PET-MR.

A technical effect of at least one embodiment may include more quickly positioning detector heads from an NM imaging system. Another technical effect of at least one embodiment may include positioning the detector heads from an NM imaging system to receive a greater photon detection rate. Another technical effect of at least one embodiment may include positioning the detector heads from an NM imaging system so that a length of the imaging session may be reduced. Another technical effect of at least one embodiment may include the patient being exposed to a smaller dosage of radiopharmaceutical. Another technical effect of at least one embodiment may include decreasing the time in which the patient experiences discomfort.

The NM imaging system includes a plurality of detector heads (e.g., 4, 5, 6, 7, 8, 9, 10, 11, 12 or more) that are positioned about a cavity of the NM imaging system. The detector heads may be selectively positioned. For example, the detector heads may be moved along unique paths for positioning the plurality of detector heads about a region-of-interest (ROI) of an object. The detector heads may be moved by respective motors. At least some of the detector heads may be movable in an axial direction (e.g., generally toward or away from a longitudinal axis extending through the cavity) and rotatable about a respective sweep axis that extends parallel to the longitudinal axis. The detector heads may also be moved as a group. For example, a set of detector heads may be rotated as a group about the longitudinal axis. In some embodiments, only a select number of the detector heads (e.g., 3, 4, 5, 6, or 7 detector heads) may be used to obtain the images. The detector heads may have respective detector field-of-views (FOVs).

The detector heads may be moved toward or away from the object within the cavity. For example, a central longitudinal axis may extend through a geometric center of the cavity. The detector heads may be distributed about the cavity and generally face the longitudinal axis. The detector heads may be moved generally toward or generally away from the longitudinal axis. Optionally, the detector heads are rotatable about axes that extend parallel to the cavity. The detector heads may also be rotatable about a sweep axis that is parallel to the longitudinal axis.

FIG. 1 is a schematic diagram of a nuclear medicine imaging (NM) system 100. It should be noted that the arrangement of FIG. 1 is provided by way of example for illustrative purposes, and that other arrangements may be employed in various embodiments. In the illustrated embodiment, the NM imaging system 100 includes a plurality of detector assemblies 102 that are coupled (e.g., mounted) to a gantry or rotor 104 that includes a cavity 118 of the NM imaging system 100. The cavity 118 is sized and shaped to receive an object 110 therein. The cavity 118 may also be referred to as a bore. The imaging system 100 may also include a table 119 that is positioned within the cavity 118. The table 119 is configured to support the object 110, such as a patient. In other embodiments, the imaging system 100 may include a chair or similar supporting element. The detector assemblies 102 are positioned circumferentially about the cavity 118. The detector assemblies 102 may be positioned within the gantry 104 such that the detector assemblies 102 are not visible to the patient or, alternatively, at least a portion of the detector assemblies 102 may be exposed within the cavity 118.

The imaging system 100 typically includes a plurality of the detector assemblies 102. In the illustrated embodiment, each detector assembly 102 includes a movable arm (or radial beam) 114 and a detector head 116 that is coupled to the movable arm 114. The detector head 116 is configured to detect radiation emitted from the object 110 within the cavity 118. The detector head 116 is disposed at a radially-inward end or distal end 115 of the movable arm 114. The movable arm 114 is configured to move the detector head 116 axially toward and/or away from a center of the cavity 118 (and/or in other directions). To this end, the movable arm 114 may move linearly between a fully retracted position and a fully extended position. When the movable arm 114 is in the fully retracted position, the detector head 116 is at a starting position (or minimum radial position). When the movable arm 114 is in the fully extended position, the detector head 116 is at an end position (maximum radial position).

Spatial positions, orientations, and movement of the object 110 or a table within the cavity 118 may be described with reference to a longitudinal axis 191, a vertical axis (or elevation axis) 192, and a horizontal axis (or lateral axis) 193. In the illustrated embodiment, the longitudinal axis is a central longitudinal axis 191 that extends through a geometric center of the cavity 118 when viewed down the longitudinal axis 191. As used herein, the term "radial" characterizes movements, positions, and the like with reference to a general center of the cavity 118 or a position of the object within the cavity 118. The term "radial" does not require knowledge of the geometric center of the cavity or that the cavity defines a circle.

Optionally, the detector head 116 is rotatable about a sweep or unit axis 194 that is parallel to the longitudinal axis 191. Optionally, the gantry 104 is rotatable about a center of the cavity 118 (e.g., the central longitudinal axis). Accordingly, for some embodiments, the detector heads 116 are configured to (a) move toward or away from a center of the cavity 118 in a radial manner; (b) rotate about the sweep axis 194; and (c) rotate, as a group, about the center of the cavity 118. These movements may occur simultaneously, concurrently (e.g., partially overlapping), or at separate times. It is contemplated, however, that the detector head 116 may be movable in other manners.

Each detector head 116 may have a relative position with respect to the cavity 118 or a relative position with respect to the object 110. The relative position may include a spatial location (e.g., coordinates in an X, Y, Z space or a vector), a group rotational position (e.g., rotational position of the gantry 104 about the central longitudinal axis 191), and an individual rotational position (e.g., rotational position about the sweep axis 194). In some embodiments, the relative position of each detector head 116 may be defined by a length (or extension) of the movable arm 114, a rotational position of the gantry 104 (e.g., number of degrees relative to a known position), and a rotational position of the detector head 116 (e.g., number of degrees relative to a known position). Embodiments may determine a location of the object 110 within the cavity 118 and determine a desired position of each detector head 116 for imaging the ROI of the object 110.

To this end, the imaging system 100 and/or the detector heads 116 may include encoders that identify the length of the movable arm 114, the rotational position of the gantry 104, and the rotational positions of the detector heads 116. For example, each of the movable arms 114 may be operably coupled to one or more detector motors 125 that selectively controls the extension of the movable arm 114. When the detector motor 125 moves the movable arm 114, an encoder may determine a length of the movable arm 114 based on a state of the detector motor 125 (e.g., number of revolutions of a lead screw) and/or a state of the movable arm 114. Similarly, an encoder may be operably coupled to the gantry 104 and determine a rotational position of the gantry 104 relative to a stator 105. Similarly, an encoder may be operably coupled to the detector head 116 and determine a rotational position of detector head 116 relative to a base or home position.

The detector head 116 may be, for example, a semiconductor detector. For example, a semiconductor detector in various embodiments may be constructed using different materials, such as semiconductor materials, including Cadmium Zinc Telluride (CdZnTe), often referred to as CZT, Cadmium Telluride (CdTe), and Silicon (Si), among others. The detector head 116 may be particularly configured for use with, for example, nuclear medicine (NM) imaging systems, positron emission tomography (PET) imaging systems, and/or single photon emission computed tomography (SPECT) imaging systems.

Each of the detector heads 116 in various embodiments is smaller than a conventional whole body or general purpose imaging detector. A conventional imaging detector may be large enough to image most or all of a width or length of a patient's body at one time and may have a diameter or a larger dimension of approximately 50 cm or more. In contrast, each of the detector heads 116 may have dimensions of, for example, 4×28 cm and may be formed of Cadmium Zinc Telluride (CZT) tiles or modules. As another example, each of the detector heads 116 may be 8×8 cm in size and be composed of a plurality of CZT pixelated modules (not shown). For example, each module may be 4×4 cm in size and have 16×16=256 pixels (pixelated anodes). In some embodiments, each detector head 116 includes a plurality of modules, such as an array of 1×7 modules. However, different configurations and array sizes are contemplated including, for example, detector heads 116 having multiple rows of modules.

Optionally, for embodiments employing one or more parallel-hole collimators, multi-bore collimators may be constructed to be registered with pixels of the detector heads 116, which in one embodiment are CZT detectors. However, other materials may be used. Registered collimation may improve spatial resolution by detecting only photons going through one collimator bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

Each of the detector heads 116 has a detector surface or face, which is directed towards the object 110 or an (ROI) within the object 110. It should be understood that the detector heads 116 may be different sizes and/or shapes with respect to each other, such as square, rectangular, circular or other shape. An actual FOV of each of the detector heads 116 may be directly proportional to the size and shape of the respective detector head. The detector heads 116 are arranged in a set or array 120. The set 120 may be rotated as a group about the cavity 118 or, more specifically, about the central longitudinal axis 191.

Accordingly, each of the detector heads 116 may be rotated with other detector heads 116 about the central longitudinal axis 191, selectively moved radially toward or away from the object 110, and selectively rotated about a respective sweep axis 194 that extends parallel to the longitudinal axis 191. As used herein, an element or component is "selectively rotatable," "selectively movable," and the like if the element or component may be controlled in a manner that is different with respect to similar elements or components. For example, one detector head may be rotated 15° and another detector head may be rotated 10°. The phrases do not require, however, the each element or component be controlled differently. Instead, the terms "selective" or "selectively" only acknowledge that the element or component may be controlled differently.

The table 119 is configured with a support mechanism (not shown) to support and carry the object 110 in one or more of a plurality of viewing positions within the cavity 118 and relative to the detector heads 116. For example, the table 119 may be operably coupled to one or more motors 145. The motor(s) 145 may be configured to move the table 119 along the central longitudinal axis 191, along the vertical axis 192, and also along the horizontal axis 193. The axes 191-193 are mutually perpendicular. As such, the table 119 and the corresponding motor(s) 145 may selectively position the object 110 within the cavity 118. Similar to the detector heads, an encoder 146 or other device may determine a position of the table 119 within the cavity 118.

In the illustrated embodiment, the gantry 104 is circular or donut-shaped. In other embodiments, however, the gantry 104 may be configured to have other shapes. For example, the gantry 104 may be formed as a closed ring or circle, or as an open arc or arch which allows the object 110 to be easily accessed while imaging and facilitates loading and unloading of the object 110. The gantry 104 may be rotated about the central longitudinal axis 191.

A control system 130 may control the movement and the positioning of the table 119, the detector heads 116, the gantry 104 and/or other components. The control system 130 may have a gantry motion controller 132, a table motion controller 134, a detector motion controller 136, and a body-contour estimator 138. The motion controllers 132, 134, 136 may be automatically commanded by at least one system processing unit 150, manually controlled by an operator, or a combination thereof. As used herein, "at least one processor" may include one or more processors, such as the processing unit 150, the motion controllers 132, 134, 136, and the body-contour estimator 138. The control system 130 may include the at least one processor.

As described herein, the body-contour estimator 138 is configured to determine a body contour of the object 110 within the cavity 118. The body contour represents an exterior surface or boundary of the object and may be determined using at least one of a number of possible methods. For instance, a two-dimensional or three-dimensional body contour may be determined using light-emitting diodes (LEDs), lasers, sensors, and/or cameras. Such embodiments are described in U.S. application Ser. No. 15/724,606, filed on Oct. 4, 2017, and U.S. Patent Application Publication No. 2015-0327831A1, each of which is incorporated herein by reference for the purposes of understanding processes for determining a body contour. A body contour may also be determined using proximity sensor device (PSDs) attached to the detector heads. For instance, several detector heads having respective PSDs attached thereto may be moved toward the object. When the PSD of a detector head engages the object or is within a predetermined distance from the object, the PSD is activated and communicates a signal to the body-contour estimator. The body-contour estimator may use the positions of the detector heads when the PSDs are activated to estimate a body contour. For multi-modality imaging systems, the body contour may be at least partially based on image data from the other modality. For instance, the other modality may acquire CT image data. The body contour may be at least partially based on the CT image data.

The gantry motion controller 132 is configured to move the detector heads 116 with respect to the object 110. The gantry motion controller 132 may control one or more motors (not shown) to move the detector heads 116 as a group about the central longitudinal axis 191. In some embodiments, the gantry motion controller 132 may cause the gantry 104 to rotate about the axis 191, which may include motion of less than or up to 180°. It is contemplated, however, that the gantry 104 may rotate more than 180°.

The table motion controller 134 may move the table 119 to position the object 110 relative to the detector heads 116. The table 119 may be moved in up-down directions along the vertical axis 192, in-out directions along the central longitudinal axis 191, and lateral directions along the horizontal axis 193. The detector motion controller 136 may control movement of each of the detector heads 116 to move together as a group or individually. The detector motion controller 136 also may control movement of the detector heads 116 in some embodiments to move closer to and farther from a surface (as defined by the body contour) of the object 110, such as by controlling translating movement of the detector heads 116 towards or away from the object 110 (e.g., sliding or telescoping movement). The detector motion controller 136 may also control the pivoting or rotating movement of the detector heads 116. For example, one or more of the detector heads 116 may be rotated about the sweep axis 194 to view the object 110 from a plurality of angular orientations.

In other embodiments, however, the detector heads may be capable of moving in additional directions. For example, the detector heads may be capable of translating in a direction that is parallel to the central longitudinal axis 191 and/or rotating about a radial axis that extends toward the central longitudinal axis 191. Embodiments may also be configured to move the detector heads in directions other than radial or longitudinal. For example, the detector heads may be coupled to robotic arms having joints that allow the detector head to be manipulated into any desired position that faces the patient.

It should be noted that motion of one or more detector heads 116 may be in directions other than strictly axially or radially, and motions in several motion directions may be used in various embodiment. The term "motion controller" may be used to indicate a collective name for all motion controllers. It should be noted that the various motion controllers may be combined, for example, the detector motion controller 136, the table motion controller 134, and the gantry motion controller 132 may be combined to position the detector heads 116 relative to the object for imaging the object. One or more of the motion controllers may have a processor and a storage medium (e.g., memory) that is configured to store programmed instructions accessible by the processor. The processor is configured to execute one or more operations based on the programmed instructions. For example, the processor may transmit command signals to one or more of the motors. Optionally, a collimator of a detector head 116 may be movable. In such embodiments, a collimator motion controller (not shown) may be provided that is configured to control motion of the collimator.

The components, circuitry, and systems responsible for positioning the object and the detector heads may be collectively referred to as a positioning sub-system 140. For example, the positioning sub-system 140 may include the gantry motion controller 132, the table-motion controller 134, the detector-motion controller 136, and the body-contour estimator 138. The positioning sub-system 140 also includes the motors 125 and the motor(s) 145. The motion controller 136 is configured to control the detector motor 125 to position the detector head 116 for detecting radiation emitted from the object 110.

The positioning sub-system 140 is configured to move the object and/or the detector heads so that the object and detector heads have an acquisition configuration. The acquisition configuration describes the different positions or states of the various elements for acquiring image data. Each acquisition configuration may have (1) a designated position (e.g., longitudinal position, vertical position, and lateral position) of the table within the cavity; (2) a designated rotational orientation of the gantry (or a designated rotational orientation of the array of detector assemblies); (3) a designated number of detector heads that will detect radiation from the object, referred to as primary detector heads, which may include all of the detector heads or fewer detector heads; (4) designated positions (e.g., radial position or X, Y, Z coordinates) of the detector heads within the cavity; and/or (5) designated rotational orientations about respective sweep axes.

Optionally, the positioning sub-system 140 also includes a proximity sensor device (PSD) 142 coupled to a respective detector head 116. The PSD 142 is configured to be activated when the PSD 142 engages the object 110 or when the PSD 142 is within a predetermined distance from the object 110, such as one centimeter or less. In certain embodiments, the PSD 142 is a pressure sensitive device. In response to being activated, the PSD 142 is configured to transmit a command signal to stop the detector head 116 moving toward the object 110. For example, the command signal may be sent to the motion controller 136, which may then transmit a command signal to the detector motor 125 to stop moving toward the object 110. Alternatively, the command signal may be sent directly to the detector motor 125, bypassing the motion controller. Examples of PSDs that may be used in one or more embodiments are described in U.S. Pat. No. 5,486,700 and U.S. Patent Application Publication Nos. 2013/0163728 and 2016/0007941, each of which is incorporated herein by reference in its entirety.

Optionally, a position of the detector head 116 when the PSD 142 is activated may be used to determine the body contour. For example, when the PSD 142 is activated, the body-contour estimator 138 may communicate to the processing unit 150 that a portion of the exterior surface of the object is a designated distance (e.g., one centimeter) in front of the detector head 116.

Prior to acquiring an image of the object 110 or a portion of the object 110, the detector heads 116, the gantry 104, and the table 119 may be adjusted, such as to first or initial imaging positions, as well as subsequent imaging positions. The detector heads 116 may each be positioned to image a portion of the object 110. Alternatively, for example in a case of a small size object 110, one or more of the detector heads 116 may not be used to acquire data. Positioning may be accomplished manually by the operator and/or automatically, which may include using, for example, image data such as other images acquired before the current acquisition, such as by another imaging modality such as X-ray Computed Tomography (CT), MM, X-Ray, PET or ultrasound. In some embodiments, the additional information for positioning, such as the other images, may be acquired by the same system, such as in a hybrid system (e.g., a SPECT/CT system). Additionally, the detector heads 116 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

The detector heads 116, the gantry 104, and/or the table 119 are may be positioned for acquiring persistence images and diagnostic images. Persistence images (or scout images) have a lower quality than diagnostic images and may be used to determine a location of the ROI. After the table 119 (or object 110) is positioned for diagnostic imaging, the detector heads 116, the gantry 104, and/or the table 119 may be positioned to acquire three-dimensional (3D) SPECT images. The image data acquired by each detector head 116 may be combined and reconstructed into a composite image or 3D images in various embodiments.

In various embodiments, a data acquisition system (DAS) 160 receives electrical signal data produced by the detector heads 116 and converts this data into digital signals for subsequent processing. However, in various embodiments, digital signals are generated by the detector heads 116. An image reconstruction device 162 (which may be a processing device or computer) and a data storage device (or memory) 164 may be provided in addition to the processing unit 150.

It should be noted that one or more functions related to one or more of data acquisition, motion control, data processing and image reconstruction may be accomplished through hardware, software, and/or by shared processing resources, which may be located within or near the imaging system 100, or may be located remotely. Additionally, a user input device 166 (e.g., mouse, keyboard, touchpad, touchscreen, and the like) may be provided to receive user inputs (e.g., control commands), as well as a display 168 for displaying screens to the user. The DAS 160 receives the acquired image data from the detector heads 116 together with the relative positions of the detector heads 116 for reconstruction of images.

In various embodiments, the detector head may include an array of pixelated anodes, and may generate different signals depending on the location of where a photon is absorbed in the volume of the detector under a surface of the detector. The volumes of the detector under the pixelated anodes are defined as voxels (not shown). For each pixelated anode, the detector has a corresponding voxel. The absorption of photons by certain voxels corresponding to particular pixelated anodes results in charges generated that may be counted. The counts may be correlated to particular locations and used to construct an image or a composite image.

Figure 2:
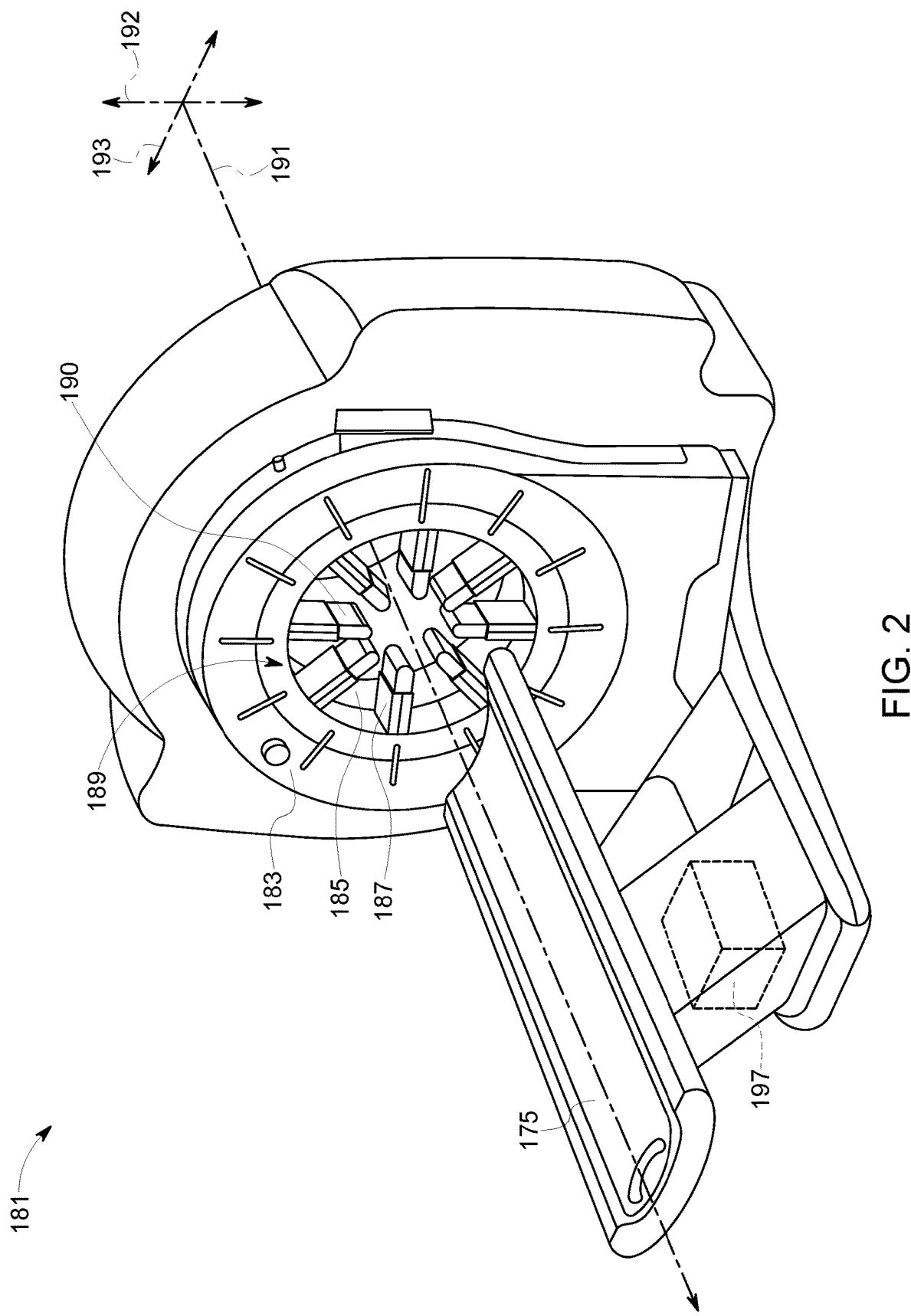
FIG. 2 is a perspective view of a NM imaging system in accordance with an embodiment.

FIG. 2 is a perspective view of a nuclear medicine (NM) imaging system 181. The NM imaging system 181 may include elements that are similar or identical to the elements of the NM imaging system 100. It should be noted that the arrangement of FIG. 2 is provided by way of example for illustrative purposes, and that other arrangements may be employed in various embodiments. The NM imaging system 181 of FIG. 2 is configured as a SPECT imaging system. In the illustrated embodiment, the NM imaging system 181 has a gantry 183 including a cavity 185 that is sized and shaped to receive an object therein. In particular embodiments, the object is a patient (e.g., human or animal). The cavity 185 is oriented relative to mutually perpendicular longitudinal, vertical, and horizontal axes 191, 192, 193. The cavity 185 extends lengthwise along the longitudinal axis 191. In the illustrated embodiment, the longitudinal axis 191 is a central longitudinal axis that extends through a geometric center of the cavity 185. The vertical axis 192 extends parallel to a gravitational force in FIG. 2. However, for other configurations of the NM imaging system, the vertical axis 192 may not extend parallel to the gravitational force. Optionally, the NM imaging system 100 may adjoin or be positioned adjacent to a computed tomography (CT) imaging system (not shown). The gantry 183 has a discrete housing and is configured to rotate at a rotational speed in one or both directions about the longitudinal axis 191.

The NM imaging system 181 also includes a plurality of detector assemblies 187. As shown, the detector assemblies 187 are positioned in an array 189 in which the detector assemblies 187 are distributed at least partially around the cavity 185. In the illustrated embodiment, the detector assemblies 187 are evenly distributed circumferentially about the longitudinal axis 191. Each of the detector assemblies 187 in the array 189 includes a movable arm (not shown) and a detector head 190 that is coupled to the movable arm. The movable arm is configured to move the detector head 190 toward and away from the object within the cavity 185.

Also shown, the NM imaging system 181 includes a movable table 175. The movable table 175 is configured to receive the object (e.g., a patient) and move the object into the cavity 185 along the longitudinal axis 191. In some embodiments, the movable table 175 may move in one or both directions along the vertical axis 192 and in one or both directions along the horizontal axis 193. Movement along the vertical axis 192 and the horizontal axis 193 may occur simultaneously or in separate movements (e.g., first up, then over). As set forth herein, the NM imaging system 181 may move the detector heads 190 and the movable table 175 so that a series of detector heads 190 are positioned in a dense group that borders the object.

The movable table 175 is operably coupled to one or more motors 197 that are controlled by one or more processors (not shown). The motors 197 are configured to move the movable table 175 to a designated position. For example, the processor(s) may control the motors 197 and the detector assemblies 187 so that the object has a desired position relative to the detector heads 190.

Figure 19:
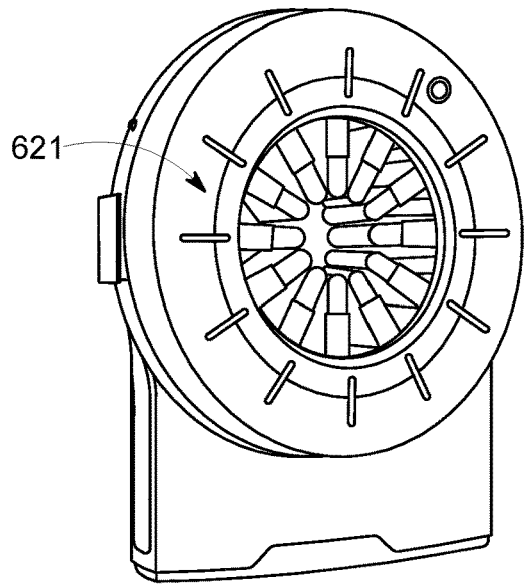
FIG. 19 is a perspective view of an NM imaging system in which the detector heads are positioned for a brain protocol.
Figure 20:
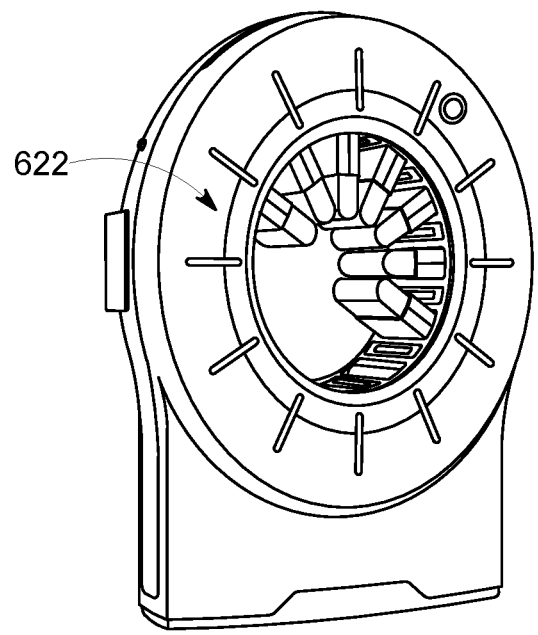
FIG. 20 is a perspective view of an NM imaging system in which the detector heads are positioned for a cardiac protocol.
Figure 21:
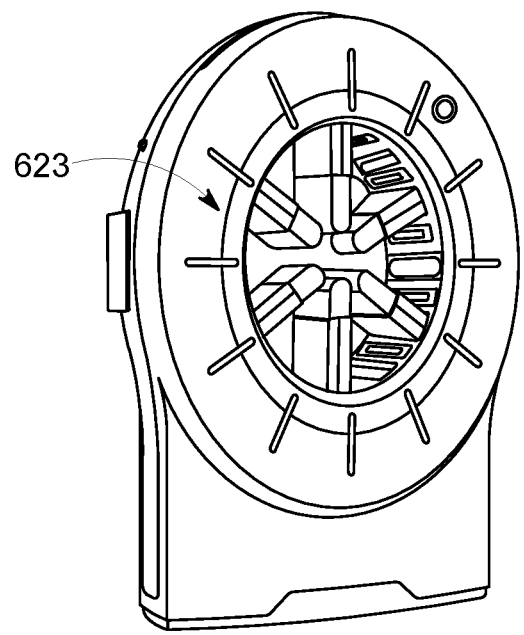
FIG. 21 is a perspective view of an NM imaging system in which the detector heads are positioned for an extremities protocol.

FIGS. 19-21 illustrate different acquisition configurations that may be used by embodiments set forth herein. Embodiments may have pre-defined acquisition configurations based upon a desired protocol and/or organs of interest. (1) a designated position (e.g., longitudinal position, vertical position, and lateral position) of the table within the cavity; (2) a designated rotational orientation of the gantry (or a designated rotational orientation of the array of detector assemblies); (3) a designated number of detector heads that will detect radiation from the object, referred to as primary detector heads, which may include all of the detector heads or fewer detector heads; (4) designated positions (e.g., radial position or X, Y, Z coordinates) of the detector heads within the cavity; and/or (5) designated rotational orientations about respective sweep axes.

FIG. 19 illustrates an acquisition configuration 621 for a brain protocol. For the brain protocol, all of the detector heads may be configured to detect radiation.

FIG. 21 illustrates an acquisition configuration 623 for an extremities protocol. In an extremities protocol, a designated number of detector heads (e.g., between three and six) may be positioned for scanning the desired region of interest. Unlike the positions of the detector heads for the brain protocol, fewer detector heads may be used in the extremities protocol and may have radial positions that are closer to a center of the cavity. FIG. 20 illustrates an acquisition configuration 622 for a cardiac protocol. In a cardiac protocol, several detector heads (e.g., three to eight detector heads) may be positioned adjacent to a side of the patient where the heart is located. As shown in FIG. 20, the secondary detector heads are not used to acquire image data.

In other embodiments, the secondary detector heads may acquire image data. Image data from secondary detector heads may contribute to the reconstructed image of the ROI. In some embodiments, the image data from the secondary detector heads may be used to determine background radiation from other parts of the body other than the ROI. In some embodiments, the image data from the secondary detector heads may be used to determine a position of the ROI relative to other regions in the body.

Optionally, healthcare-providers may choose to purchase systems that do not use each and every possible detector heads. For example, healthcare providers that are dedicated to evaluating cardiac conditions, the imaging system may only have the detector heads that are extended in FIG. 20. As another example, due to the costs of the detector heads, a healthcare-provider for children may acquire an imaging system having only the detector heads that are extended in FIG. 21, because additional detector heads are not necessary. More specifically, a child's body is smaller than an adult's body. As such, each detector head covers more of a child's body and may be permitted to move closer to the child's body.

Optionally, for one or more cardiac protocols, an arm of the patient may be removed from a side of the torso of the patient, thereby allowing one or more detector heads to be positioned closer to the ROI. Optionally, a patient may be inserted into the cavity "feet first." Also optionally, one or more accessories (e.g., supports) may be used to support the patient. For example, a local support may be positioned proximate to the patient such that the arm of the patient may rest upon the local support during imaging. The local support may be positioned outside of the cavity. As another example, a local support may be positioned between the table and the patient (e.g., a torso of the patient), thereby changing an orientation of the body contour with respect to the table.

Figure 3:
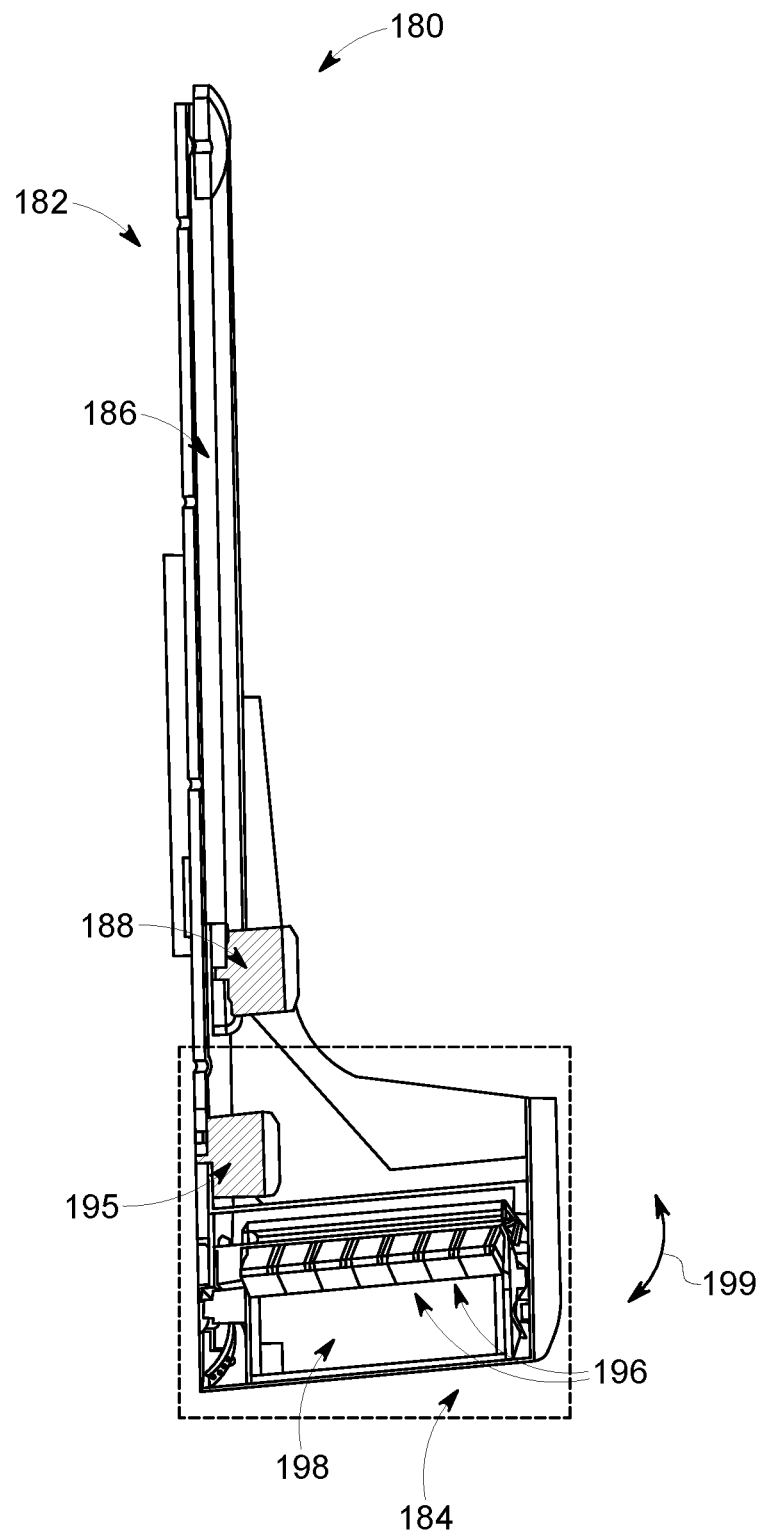
FIG. 3 is a perspective view of a detector assembly in accordance with an embodiment.

FIG. 3 illustrates a detector assembly 180 in accordance with an embodiment. The detector assembly 180 may be used as the detector assembly 102 (FIG. 1) of the imaging system 100 (FIG. 1) or as the detector assembly 187 (FIG. 2) of the NM imaging system 181 (FIG. 2). The detector assembly 180 includes a movable arm 182 that is configured to couple to a gantry or rotor (not shown), such as the gantry 104 (FIG. 1), and a detector head 184. The movable arm 182 includes a rail 186 and a detector motor 188. The detector motor 188 may also form part of a positioning sub-system as described herein. The detector motor 188 controls the movement of the detector head 184 by extending or retracting the detector head 184 along the rail 186. In such embodiments, the detector head 184 moves in a linear manner. The movable arm 182 may move telescopically. Optionally, the movable arm 182 and/or the detector head 184 can include covers that allow it to extend and contract as it moves radially in and out.

The detector head 184 includes a sweep motor 195, detector elements 196, and a collimator 198. The detector elements 196 can be CZT modules or other detector element modules discussed throughout for detecting imaging data. Sweep motor 195 controls the rotation angle of the detector head 184 in relation to a sweep axis, such as the sweep axis 194 (FIG. 1), or other reference point. A sweep motion 199 of the detector head 184 is shown in FIG. 3. A detector motion controller, such as the controller 136 (FIG. 1), can provide instruction and control to either or both of the detector motor 188 or the sweep motor 195. Thus, each detector assembly 180 is independently controllable to increase or decrease a length of the detector assembly 180

(or the movable arm 182) and independently controllable for a rotational position of the detector head 184. The detector motor 188 and the sweep motor 195 can be two separate motors. Alternatively, the functionality of the two motors may be provided by one motor.

Figure 4:
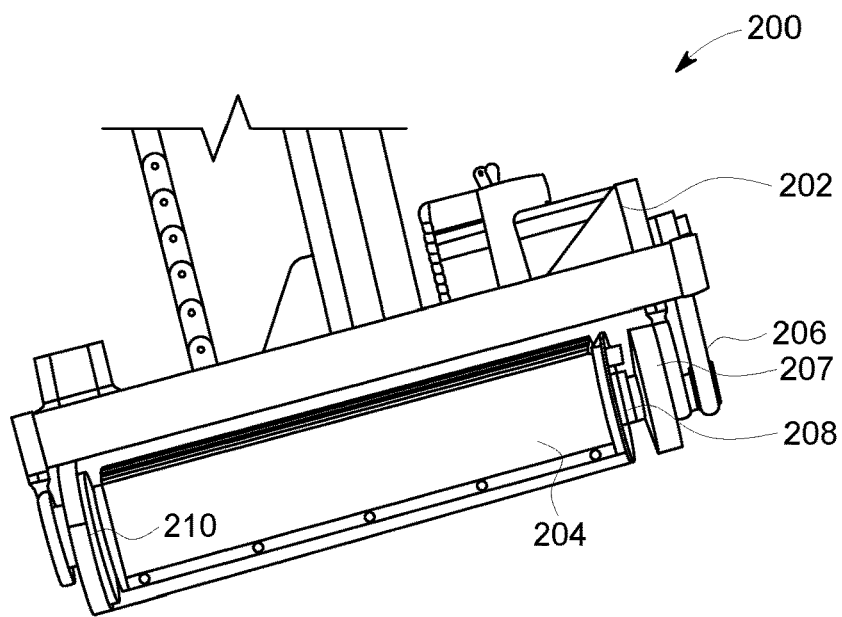
FIG. 4 provides a perspective view of a detector head in accordance with an embodiment.
Figure 5:
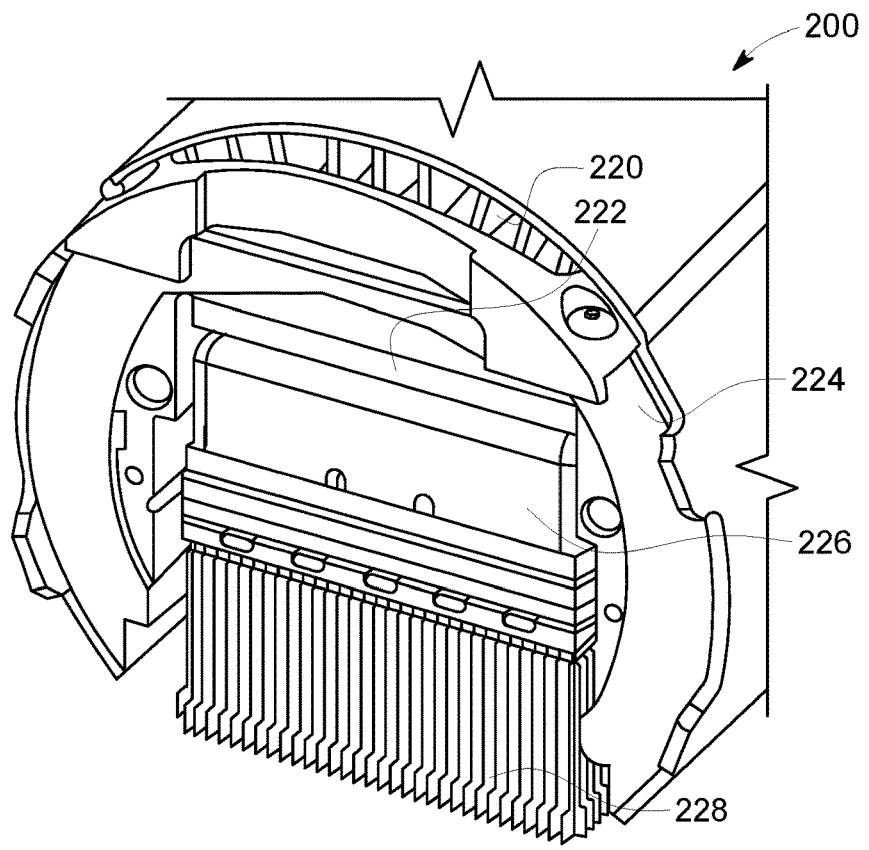
FIG. 5 shows a sectional view of the detector head of FIG. 4.

FIG. 4 is a perspective view of a detector head 200 formed in accordance with various embodiments, and FIG. 5 is a sectional view of the detector head 200. The detector head 200 may be used as part of the detector assembly 102 (FIG. 1), the detector assembly 187 (FIG. 2), or the detector assembly 180 (FIG. 3). As shown in FIG. 4, the detector head 200 includes a stepper motor 202 that may be utilized to rotate the detector head 200. It may be noted that motors other than stepper motors may be used in various embodiments. Generally, "step-and-shoot" motion may be employed in various embodiments. In step-and-shoot motion, the detector head 200 is rapidly pivoted, and then remains stationary during data collection. Step-and-shoot motion may be utilized in various embodiments to eliminate or reduce power transients and/or other electronic noise associated with activation of electrical motors. Use of step-and-shoot motion may also be utilized to eliminate orientation uncertainties associated with each collected photon.

However, it may be noted that, in various embodiments, with fine orientation encoders, and frequent sampling of the orientation encoders, detector aiming may be associated with each detected photon to sufficient accuracy even if the detectors are continuously pivoting during data acquisition. The detector head 200, for example, may include a shield, a processing board, a detector (e.g., a CZT detector) and a collimator 204. The detector head 200 also includes a gear 206 coupling the stepper motor 202 to the other components, as well as a slip ring 207 (configured to allow for transfer of signals between the rotating components and non-rotating components) and a multiplex board 208. In the illustrated embodiment, the detector head 200 also includes an air channel 210 configured to provide cooling to components of the detector head 200.

Also shown in FIG. 5, the detector head 200 includes a heat sink 220, a printed circuit board 222 (which may incorporate one or more elements of the motion controller or one or more elements of the processing unit), a lead shielding 224, a CZT photon detector 226, and a collimator 228 that is registered to the photon detector 226 in the illustrated embodiment. Additional details and discussion regarding detector heads is provided in U.S. patent application Ser. No. 14/671,039, entitled "Reduced Airborne Contamination Detector Heads," filed Mar. 27, 2015, the subject matter of which is incorporated herein by reference in its entirety.

Figure 6:
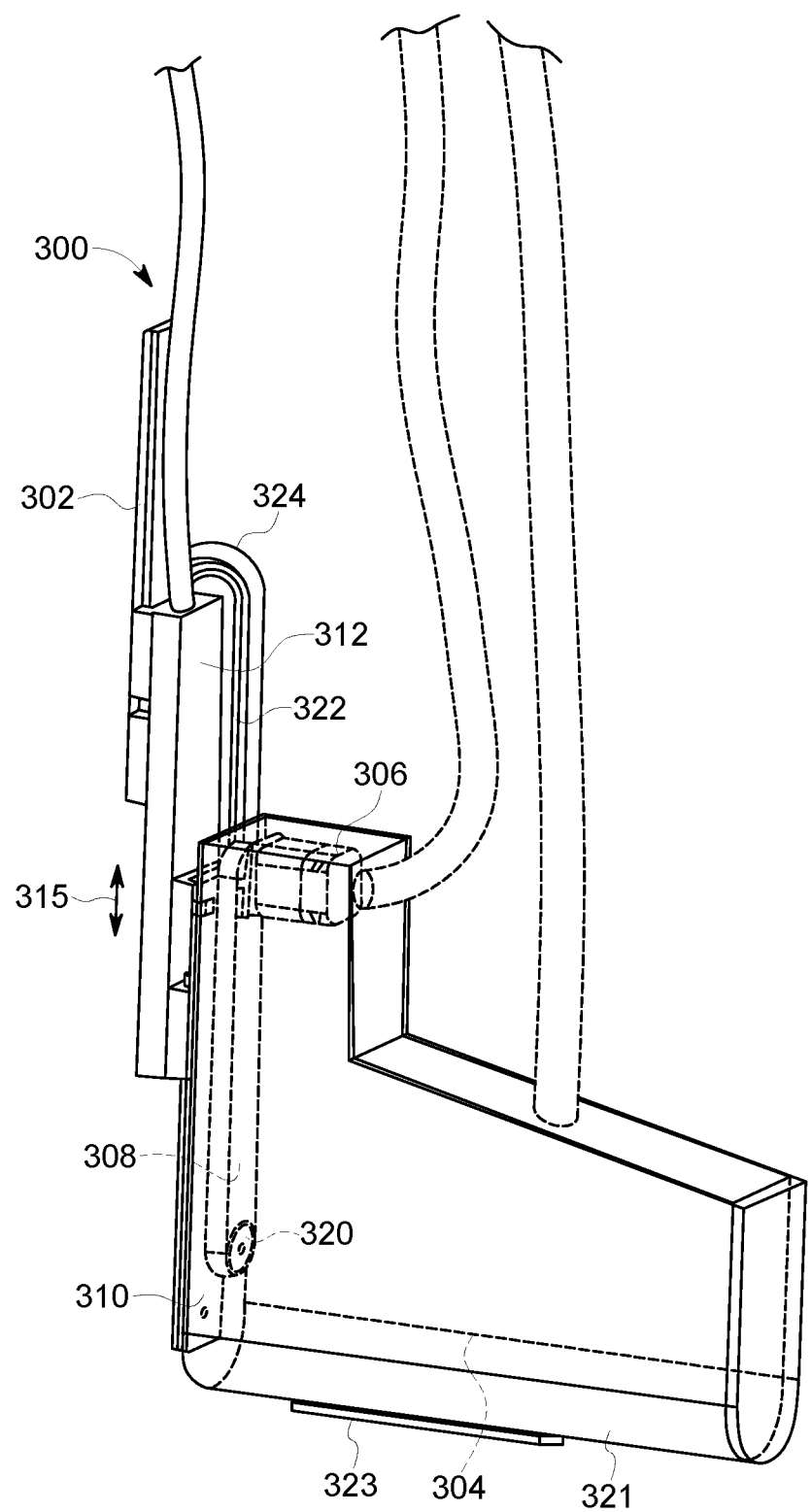
FIG. 6 is a perspective view of a detector assembly in an extended position in accordance with various embodiments.
Figure 7:
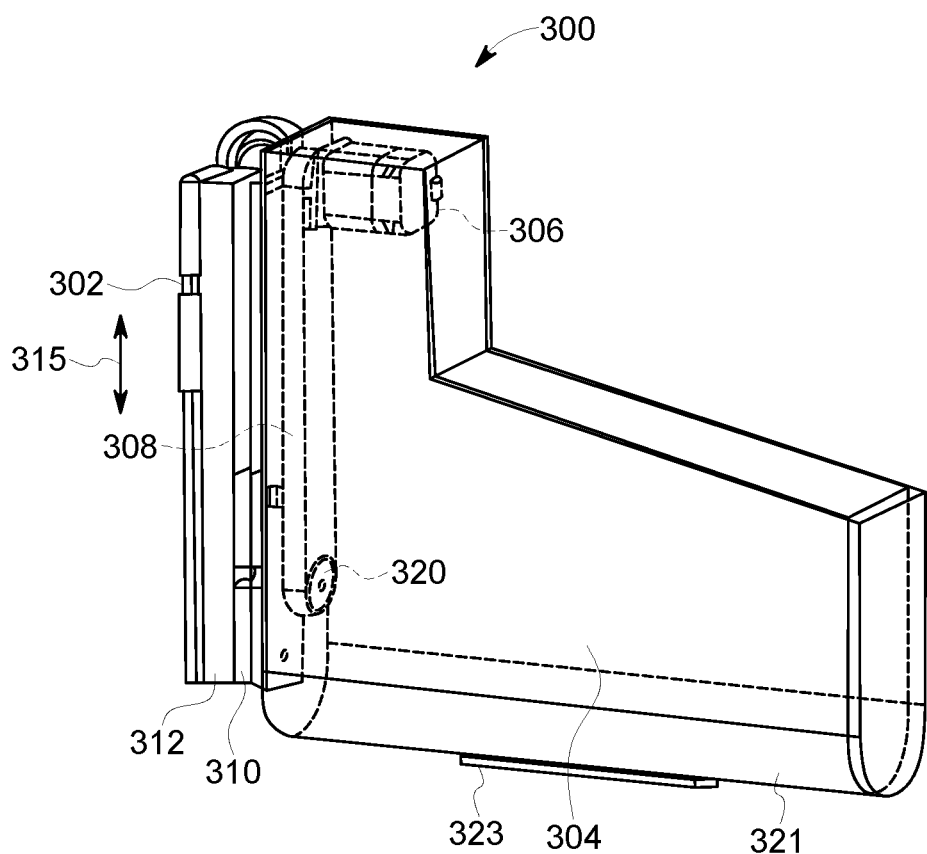
FIG. 7 is a perspective view of the detector assembly of FIG. 6 in a retracted position.

Various embodiments may utilize movable arms that are arranged in telescopic configurations to provide for a desired range of motion in a compact package. FIG. 6 provides a perspective view of a detector assembly 300 in an extended position, and FIG. 7 provides a perspective view of the detector assembly 300 in a retracted position. The detector assembly 300 may include features that are similar or identical to the detector assembly 102 (FIG. 1), the detector assembly 187 (FIG. 2), the detector assembly 180 (FIG. 3) and may be used with the NM imaging system 100 (FIG. 1) or the NM imaging system 181 (FIG. 2). As seen in FIGS. 6 and 7, the detector assembly 300 includes an arm base 302, a detector head 304, a detector motor 306, and a detector head belt 308.

The detector head 304 includes a carrier section 310 that is slidably coupled to the arm base 302 and configured to be movable along an axial direction 315 in the cavity relative to the arm base 302. Thus, the detector head 304 may be articulated radially inwardly (toward the center of the cavity) or radially outwardly (away from the center of the cavity) to place the detector head 304 in a desired position for imaging. It may be noted that the carrier section 310 and the arm base 302 may be directly or indirectly slidably coupled to each other. For example, in some embodiments, the carrier section 310 and arm base 302 may be directly slidably coupled to each other, for instance, with one of the carrier section 310 or arm base 302 including a guide that slidably accepts a rail of the other. In other embodiments, for increased compactness in the retracted position, the detector assembly 300 may be configured as a telescoping assembly with an intermediate member (e.g., slider block 312) interposed between the arm base 302 and carrier section 310, with the intermediate member slidably coupled to the arm base 302 and carrier section 310 separately, providing an example of an indirect slidable coupling between the arm base 302 and carrier section 310.

As seen in FIG. 6, the detector head 304 may be understood as being distally positioned (e.g., positioned more radially inwardly than the arm base 302). One or more detectors (e.g., one or more CZT detectors), which may be pivoted or tilted within the detector head 304, may be positioned in a distal portion of the detector head 304. It may be noted that the detector head 304 may include one or more shielding members (e.g., for shielding electronics of a photon detector from radiation), and may be configured to provide cooling (e.g., by passing a flow of air over cooling fins) to dissipate heat generated by electronics associated with the detectors. The detector head 304 may also include one or more PSDs.

The detector head 304 has a housing 321. The housing 321 defines an exterior of the detector head 304. In some embodiments, the housing 321 may engage or be positioned immediately adjacent to the housings 321 of other detector heads 304. Optionally, a proximity sensor device (PSD) 323 may be coupled to the housing 321 and positioned such that the PSD engages the object or patient.

In various embodiments, the detector motor 306 is operably coupled to at least one of the detector head 304 or the arm base 302. In the embodiment depicted in FIGS. 6 and 7, the detector motor 306 is mounted to the carrier section 310 of the detector head 304. Generally, the detector motor 306 is used to drive the detector head belt 308 to articulate the detector head 304 radially (e.g., inwardly toward the center of the cavity or outwardly away from the center of the cavity). For example, a drive shaft of the detector motor 306 may be rotated to drive the detector head belt 308. The detector motor 306 may also be used to help secure or maintain the detector head belt 308 in a desired position (e.g., by being prevented or inhibited from rotating). It may be noted that, while a motor and belt are used in the depicted embodiment (e.g., detector motor 306 is utilized to drive the detector head belt 308 and to articulate the detector head 304 radially), other devices, systems, or mechanisms may be utilized to articulate the detector head 304 radially in other embodiments.

The depicted detector head belt 308 is operably coupled to the detector motor 306 and to the carrier section 310 of the detector head 304, with rotation of the detector motor 306 (e.g., rotation of a drive or output shaft of the axial motion motor) causing movement of the detector head 304 along the axial direction 315. In the illustrated embodiment, the detector head belt 308 passes around a drive shaft and/or gear of the detector motor 306 and around a detector head gear 320 mounted to the carrier section 310. The depicted detector head gear 320 is mounted to an opposite end of the carrier section 310 than the axial motion motor, with the detector head belt 308 extending along most or all of the length of the carrier section 310 in the axial direction 315.

As mentioned above, for increased compactness in the retracted position, the detector assembly 300 may be configured as a telescoping assembly with an intermediate member (e.g., slider block 312) interposed between the arm base 302 and carrier section 310, with the intermediate member slidably coupled to the arm base 302 and carrier section 310 separately, providing an example of an indirect slidable coupling between the arm base 302 and carrier section 310.

As seen in FIG. 6, the detector assembly 300 includes a slider block 312 interposed between the detector head 304 (e.g., the carrier section 310 of the detector head 304) and the arm base 302. The slider block 312 is slidably coupled to the arm base 302 and configured to be moveable in the axial direction 315 with respect to the arm base 302. For example, one of the slider block 312 and arm base 302 may include a guide that accepts a rail of the other. Also, the carrier section 310 of the detector head 304 is slidably coupled to the slider block 312 and configured moveable in the axial direction 315 with respect to the slider block 312. For example, one of the slider block 312 and carrier section 310 may include a guide that accepts a rail of the other.

In various embodiments, one or more belts may be fixed or coupled to the one or more of the arm base 302, slider block 312, or carrier section 310 to articulate the detector head 304 in the axial direction 315, or to articulate the detector assembly 300 between extended and retracted positions.

Figure 8:
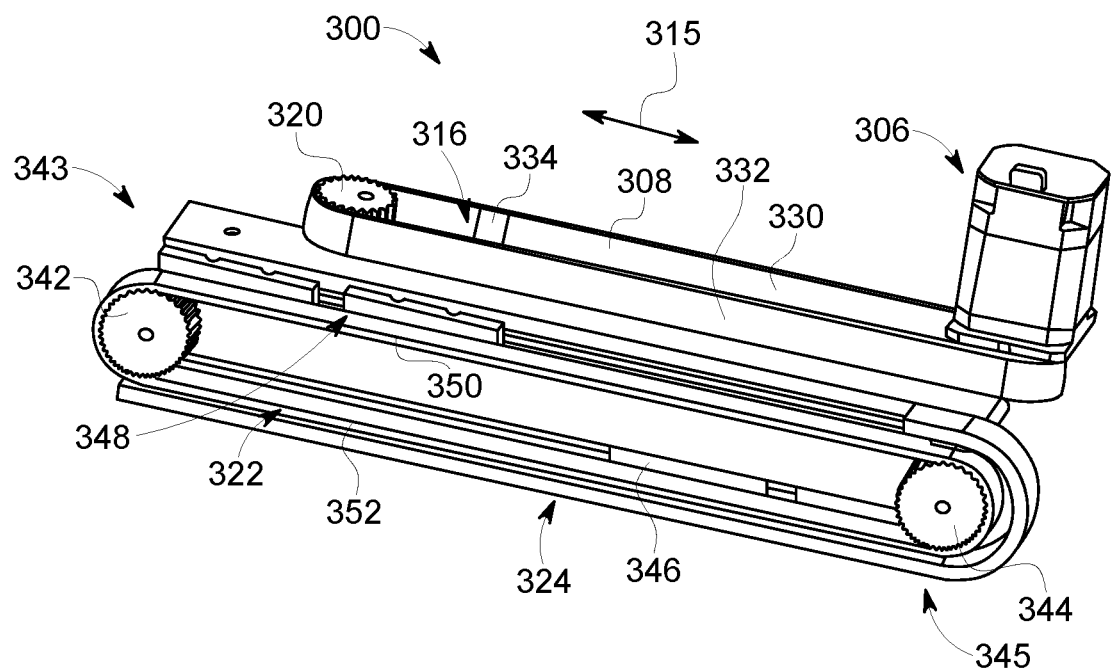
FIG. 8 is a side perspective view of the detector assembly of FIG. 6.

FIG. 8 provides a side perspective view of a portion of the detector assembly 300. The slider block 312 is fixed to the detector head belt 308 at point 316. Accordingly, the slider block 312 moves in the axial direction 315 with the detector belt 308. It may be noted that portion 332 of the detector belt 308, disposed on that opposite side of detector head gear 320 from the portion 330, moves oppositely in or along the axial direction 315 as the slider block 312. The point 316 where the slider block 312 is fixed to the detector head belt 308 may be the location of mounting to a bracket or clip 334 used to fix the slider block 312 to the detector head belt 308.

As also seen in FIG. 8, the detector assembly 300 also includes an idler belt 322. The depicted idler belt 322 is mounted to idler gears 344, 342 disposed on the slider block 312 (FIG. 6). In the illustrated embodiment, the idler gears 344, 342 are mounted on opposite ends 343, 345, respectively, of the slider block 312. The idler belt 322 is fixed to the carrier section 310 at point 346 (e.g., via a clip or bracket as discussed in connection with point 316) and to the arm base 302 (FIG. 6) at point 348 (e.g., via a clip or bracket as discussed in connection with point 316). The slider block 312 moves in the axial direction 315 with a portion 350 of the idler belt 322 relative to the arm base 302. Also, the carrier section 310 moves in the axial direction 315 with a portion 352 of the idler belt 322 relative to the slider block 312. With the portion 350 and the portion 352 on opposite sides of the idler gears 344, 342, the arm base 302 and the carrier section 310 move oppositely to each other along the axial direction 315 with respect to the slider block 312. Use of the idler belt 322 thus results in about twice the total movement of the detector head 304 (FIG. 6) with respect to the arm base 302 for the same motor rotation and/or similar retracted length compared to examples that do not use the idler belt 322 and slider block 312. It may be noted that electrical cables 324 may be disposed about the idler belt 322, with the electrical cables 324 extending along with the detector head 304 to provide electrical communication with the detector head 304 in the various positions at which the detector head 304 may be disposed.

In various embodiments, all or a portion of the arm base 302, detector head 304, and/or slider block 312 may be protected or contained within a cover. The cover may telescope with the detector assembly 300 to provide coverage over a range of motion while still providing compactness in a retracted position.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

Figure 9:
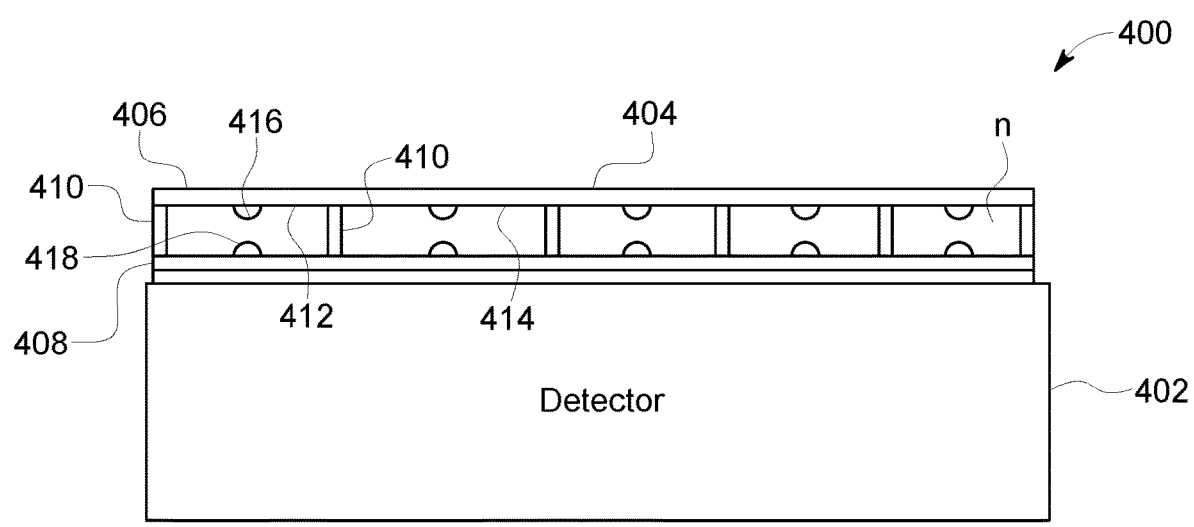
FIG. 9 is a schematic diagram of a proximity sensor device (PSD) that may be used with a detector assembly in accordance with various embodiments.

FIG. 9 is side cross-sectional view of a portion of a PSD 400 that may be incorporated into one or more embodiments described herein. For example, the PSD 400 may be similar or identical to the PSDs 142 (FIG. 1). In the illustrated embodiment, the PSD 400 has a rubber structure that is glued to a detector head 402. There is an array of contacts acting as safety switches. The PSD 400 includes a flexible upper layer 404 having multiple contacts 406. A lower layer 408 may be rigid or flexible.

In some embodiments, the upper layer 404 may be referred to as a sensing plate, and the lower layer 408 may be referred to as a lower pressure sensing plate 408. The PSD 400 also includes a plurality of flexible dividers 410. The flexible dividers 410 are utilized to form separate sensing elements, such as for example, an element 412, and element 414 . . . n, etc. Each element, such as element 412 includes a pair of metallic pads. For example, each element includes a metallic pad 416 that is coupled to a lower surface of the sensing plate 404 and a metallic pad 418 that is coupled to an upper surface of the sensing plate 408.

In operation, when an object or the patient contacts the sensing plate 404, the sensing plate 404 is depressed. Depressing the sensing plate 404 causes the metallic pad 416 to come into physical and electrical contact with the metallic pad 418 to form an electrical circuit. In operation, the electrical circuit outputs a command signal that is utilized by an NM imaging system, such as the imaging system 100 (FIG. 1), to indicate that the PSD 400 has engaged the object. More specifically, the command signal is utilized by the imaging system to stop the detector head 402 moving further toward the object and, optionally, retract the detector head 402. The PSD 400 may be configured to deactivate automatic control of moving parts of the imaging system. For example, when the PSD 400 is activated, the imaging system may stop automatic movement of a gantry, the detector heads, and/or the table.

Figure 24:
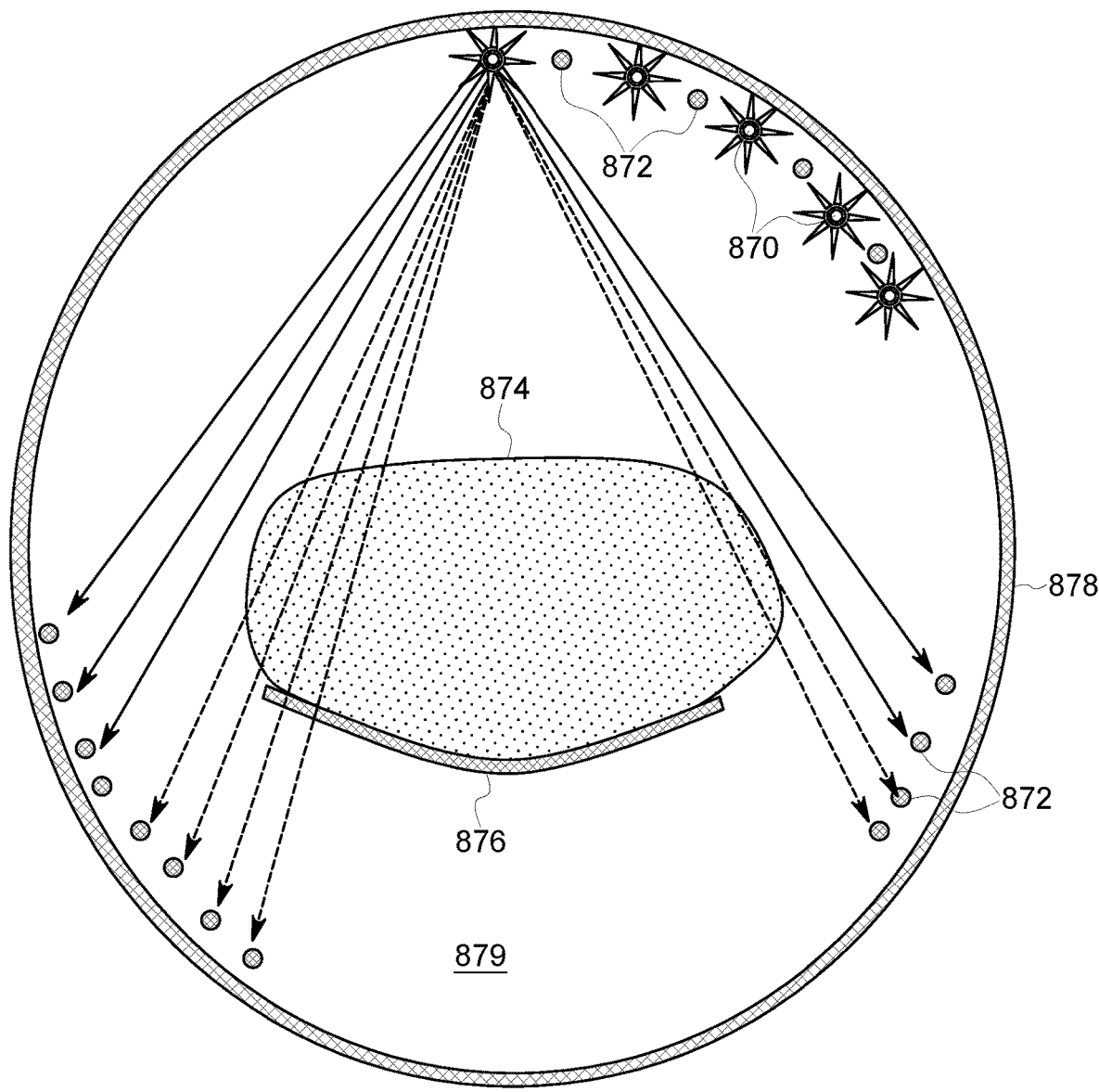
FIG. 24 illustrates an arrangement of light emitting sources and light detectors in accordance with an embodiment that may be used to determine a body contour.

FIG. 24 illustrates one method of estimating a body contour. Prior to moving the detector heads into designated imaging positions, the system (e.g., the body-contour estimator 138 (FIG. 1)) may determine a body contour. As shown, a gantry 878 includes a cavity 879 where a patient 874 may rest on a patient table 876 for an imaging session. The cross-section of the gantry 878 shown in FIG. 24 may be at an opening to the cavity 879 or a depth within the cavity 879. An array of light emitting sources 870 are positioned such that the light emitting sources 870 at least partially surround the cavity 879. Likewise, an array of light detectors 872 are positioned such that light detectors 872 at least partially surround the cavity 879. Light emitting sources 870 can be, for example, light emitting diodes (LEDs) in an embodiment. Light detectors 872 can be, for example, photo-diodes in an embodiment.

FIG. 24 shows only a partial, exemplary layout, but many useful layouts are contemplated. The light emitting sources 870 and the light detectors 872 can be positioned entirely around the cavity 879. Optionally, the light emitting sources 870 and the light detectors 872 can be placed as pairs near each other. In some embodiments, there can be double or triple the total amount of light detectors 872 around the cavity 879 compared to light emitting sources 870.

In an exemplary operation, individual light emitting sources 870 emit light at different times, which may be referred to as contour-detection events. For example, the light emitting sources 870 may emit light signals in accordance with a predetermined sequence and the light detectors 872 may detect the light signals. Only a single light emitting source 870 is emitting the light signals for the contour-detection event shown in FIG. 24. In other embodiments, multiple light emitting source 870 may be used for each contour-detection event. The solid lines in FIG. 24 indicate that emitted light signals will hit a light detector 872, because the line-of-sight was not blocked by the patient 874. The dotted lines indicate that emitted light signals will not hit a light detector 872 because the line-of-sight was blocked by the patient 874. FIG. 24, however, illustrates only one contour-detection event. After this contour-detection event, other light-emitting sources 870 may emit the light signals. For each contour-detection event, the system identifies which light detectors 872 detected the emitted light signals. The system can estimate a body contour using information from multiple contour-detection events. The body contour at one axial position of the table is now determined and, if so desired, the table 876 can be moved in the axial direction to have the system continue to estimate the body contour of additional sections of the patient.

Accordingly, for at least some embodiments, the body contour of the patient may be determined using an array of light emitters and an array of light detectors. Each of the light emitters may be configured to direct light signals toward at least one of the light detectors. The body contour may be based on identities of the light detectors that do not receive the light signals from the light emitters.

Figure 10:
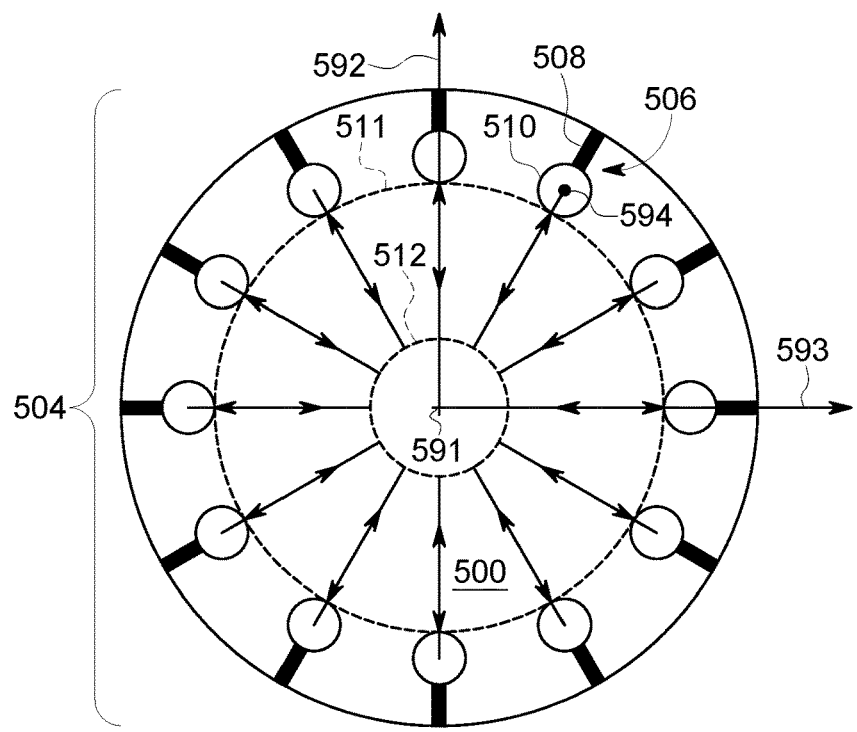
FIG. 10 is a schematic end view of a cavity having an array of detector assemblies positioned therein in accordance with an embodiment.

FIG. 10 is a schematic end view of a cavity 500 having an array of detector assemblies 506 positioned therein. The cavity and detector assemblies may be similar or identical to the cavity and detector assemblies described above. For example, the cavity 500 may be from a gantry, such as the gantry 104 or the gantry 183, and may be sized and shaped to receive an object therein. The cavity 500 is oriented relative to mutually perpendicular longitudinal, vertical, and horizontal axes 591, 592, 593. The cavity 500 extends lengthwise along the longitudinal axis 591. The detector assemblies 506 may be similar or identical to the detector assemblies 102 (FIG. 1).

Also shown, an array 504 of detector assemblies 506 are distributed around the cavity 500. In FIG. 10, the detector assemblies 506 are evenly distributed about the entire cavity 500. In other embodiments, the detector assemblies 506 are not evenly distributed and/or may not surround the entire cavity 500. As such, the array 504 may be distributed at least partially around the cavity 500.

Each of the detector assemblies 506 in the array 504 includes a movable arm 508 and a detector head 510 that is coupled to the movable arm 508. The detector head 510 may be similar or identical to one of the other detector heads described herein, such as the detector heads 114 (FIG. 1), 184 (FIG. 3), 190 (FIG. 2), 200 (FIG. 4), 304 (FIG. 6), 402 (FIG. 9). The movable arm 508 configured to move the detector head 510 toward and away from the object within the cavity 500 as indicated by the bi-directional arrows. For example, at least one processor may be configured to selectively move the detector heads by moving the movable arms so that the detector head 510 has a designated radial position. The at least one processor may also be configured to selectively rotate the detector heads 510 about a sweep axis 594, which may extend parallel to the longitudinal axis 591.

In FIG. 10, the detector heads 510 are at starting positions or at minimum radial positions. When the movable arms 508 are fully retracted, the detector heads 510 may be located at the minimum radial positions. A dashed circle 511 represents a space defined by the detector heads 510 when each of the detector heads 510 is at the minimum radial position. In FIG. 10, the space 511 has a circular cross-sectional profile. In other embodiments, however, the cross-sectional profile of the space 511 may be different (e.g., oval-like). When the movable arms 508 are fully extended, the detector heads 510 may be located at respective end positions or maximum radial positions. A dashed circle 512 represents a space defined by the detector heads 510 when each of the detector heads 510 is at the maximum radial position. In FIG. 10, the space 512 has a circular cross-sectional profile. In other embodiments, however, the cross-sectional profile of the space 512 may be different.

Figure 11:
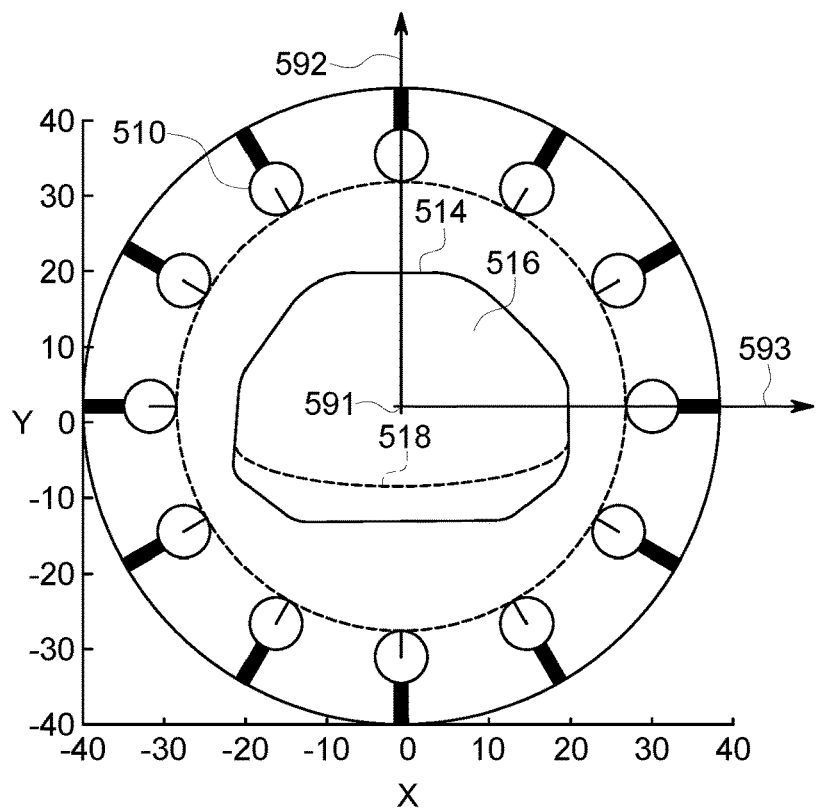
FIG. 11 is a schematic end view of the cavity of FIG. 10 having an object therein at a central position.

FIG. 11 is a schematic end view of the cavity 500 in which a body contour 514 is represented at a central position within the cavity 500. As described herein, embodiments may determine a body contour, which represents an exterior surface or boundary that the detector heads may not move beyond unless the body contour is moved. The body contour may be determined, for example, using an array of light emitting sources and light detectors, image data from other modalities, and/or PSDs. In FIG. 11, the body contour 514 represents a patient 516 and a movable table 518 that supports the patient 516. As described herein, embodiments are configured to move the body contour. For example, embodiments may move the table 518, thereby moving the patient 516 and the body contour 514. Embodiments are also configured to move at least one of the detector heads 510 such that a series of detector heads 510 are positioned in a dense group 525 (shown in FIG. 14) that borders the body contour 514. In some embodiments, the detector heads 510 from at least three adjacent detector assemblies 506 form the dense group 525.

The body contour 514 may be at the central position at a beginning of an imaging session as shown in FIG. 11. For example, after the patient rests upon the table 518, the table 518 may be moved along the longitudinal axis 591 to a longitudinal position at which the detector heads 510 are generally aligned with the ROI.

Figure 12:
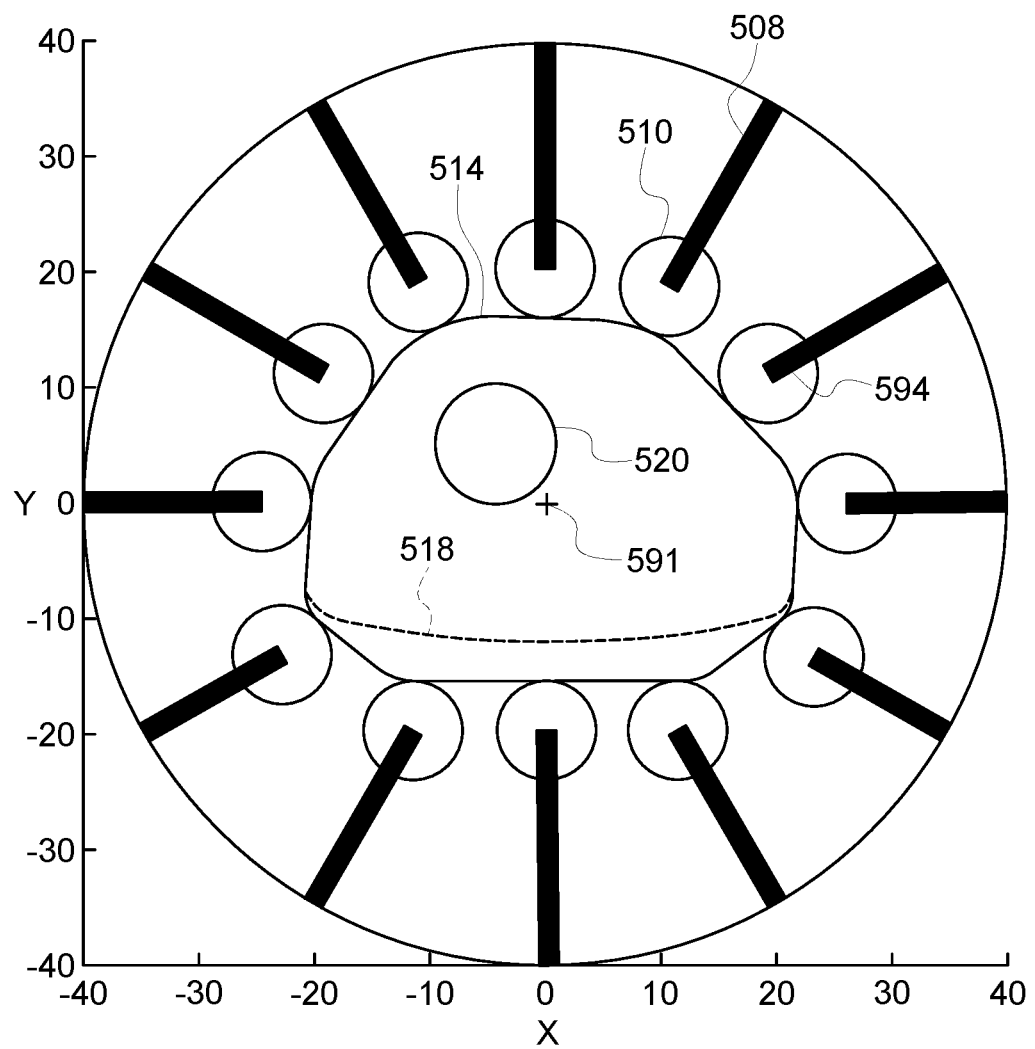
FIG. 12 is a schematic end view of the cavity of FIG. 10 in which detector heads are positioned adjacent to the object and a region of interest (ROI) is shown.
Figure 13:
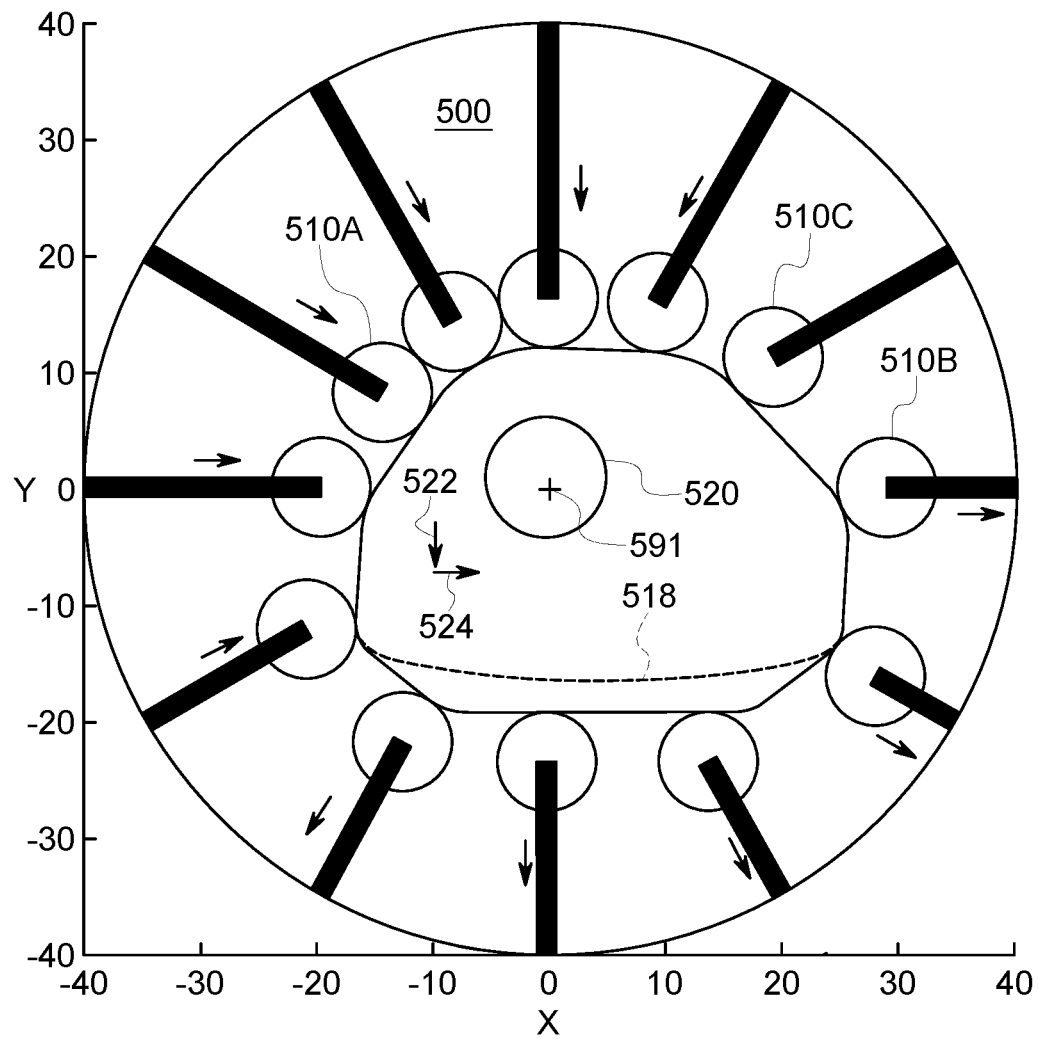
FIG. 13 is a schematic end view of the cavity of FIG. 10 in which the object and detector heads have a designated arrangement for imaging.

FIGS. 12 and 13 illustrate different arrangements in which the detector heads 510 have designated radial positions and the table 518 has a designated position. The designated position of the table 518 may include a longitudinal location along the longitudinal axis 591 (FIG. 11), a vertical location along the vertical axis 592 (FIG. 11), and a lateral location along the lateral axis 593 (FIG. 11). Although the arrangements of the detector heads 510 and the table 518 in FIGS. 12 and 13 may be used for imaging, the arrangements are used to illustrate movement of the detector heads 510 and/or the table 518.

In some embodiments, the table 518 and the detector heads 510 are moved at separate times. For example, the table 518 may be moved and the detector heads 510 may be moved after the table 518 is moved. Alternatively, the detector heads 510 may be moved and the table 518 may be moved after the detector heads 510 are moved. Alternatively, the detector heads 510 and the table 518 may be moved during overlapping time periods. In some embodiments, a plurality of iterations occur until a desired position of the ROI relative to designated detector heads is achieved. For example, the detector heads 510 may be moved, followed by the table 518, followed by the detector heads 510, followed by the table 518, and so forth. During or between moving the detector heads 510 and/or the table 518 at the different iterations, image data may be acquired of the ROI.

FIG. 12 is a schematic end view of the cavity 500 illustrating the body contour 514 and the detector heads 510 at an intermediate stage. For example, after the object is located at the central position within the cavity 500 (shown in FIG. 12), the detector heads 510 may be advanced toward the object. More specifically, the movable arms 508 may be extended or retracted so that the detector head 510 arrives at a designated radial position. As shown, the detector heads 510 are positioned immediately adjacent to the object. As used herein, an element is positioned "immediately adjacent" to another element if the two elements are abutting (e.g., contacting one another) or the two elements have a nominal gap therebetween. For example, the detector heads 510 may be engaging the patient (represented by the body contour 514) or the detector heads 510 may have a nominal gap (e.g., at most two centimeters). The nominal gap may occur due to tolerances of the NM imaging system. In some embodiments, the detector heads 510 may advance toward the patient until PSDs (not shown) are activated. An ROI 520 is also shown in FIG. 12.

In FIG. 12, each of the detector heads 510 is positioned immediately adjacent to the patient for imaging. In other embodiments, one or more of the detector heads 510 may be positioned further away from the patient. For example, one or more of the detector heads 510 may remain at the minimum radial positions.

Prior to the detector heads 510 moving toward the patient in FIG. 12, the imaging system may acquire image data that can be used to locate the ROI 520 within the body contour 514. Alternatively or in addition to the above, the detector heads 510 may acquire image data when the detector heads 510 have positions as shown in FIG. 12. The image data may be used to locate the ROI 520.

FIG. 13 is a schematic end view of the cavity 500 illustrating the body contour 514 and the detector heads 510 at an imaging stage. By comparing FIGS. 12 and 13, it can be seen that the body contour 514 has moved relative to the longitudinal axis 591. More specifically, the body contour 514 has moved a designated distance along the vertical axis (represented by arrow 522) and a designated distance along the horizontal axis (represented by arrow 524). Prior to or as the body contour 514 is moved, the detector heads 510 may also be moved. FIG. 13 illustrates one example. As shown, at least some of the detector heads 510A are extended such that the respective radial positions are moved toward the patient (as indicated by the radially-inward arrows). At least some of the detector heads 510B are withdrawn or retracted such that the respective radial positions are moved away from the patient (as indicated by the radially-outward arrows). At least one of the detector heads 510C may not move.

Optionally, the detector heads 510 may be rotated about the respective sweep axis 594 to achieve a designated position relative to the ROI 520. In some embodiments, a housing of the detector head 510 is rotated about the sweep axis 594. In other embodiments, an interior detector (not shown) within the detector head 510 is rotated about the sweep axis 594. Accordingly, a detector head is "rotated about the sweep axis" if the entire detector head is rotated about sweep axis or if an interior detector is rotated about the sweep axis.

Figure 14:
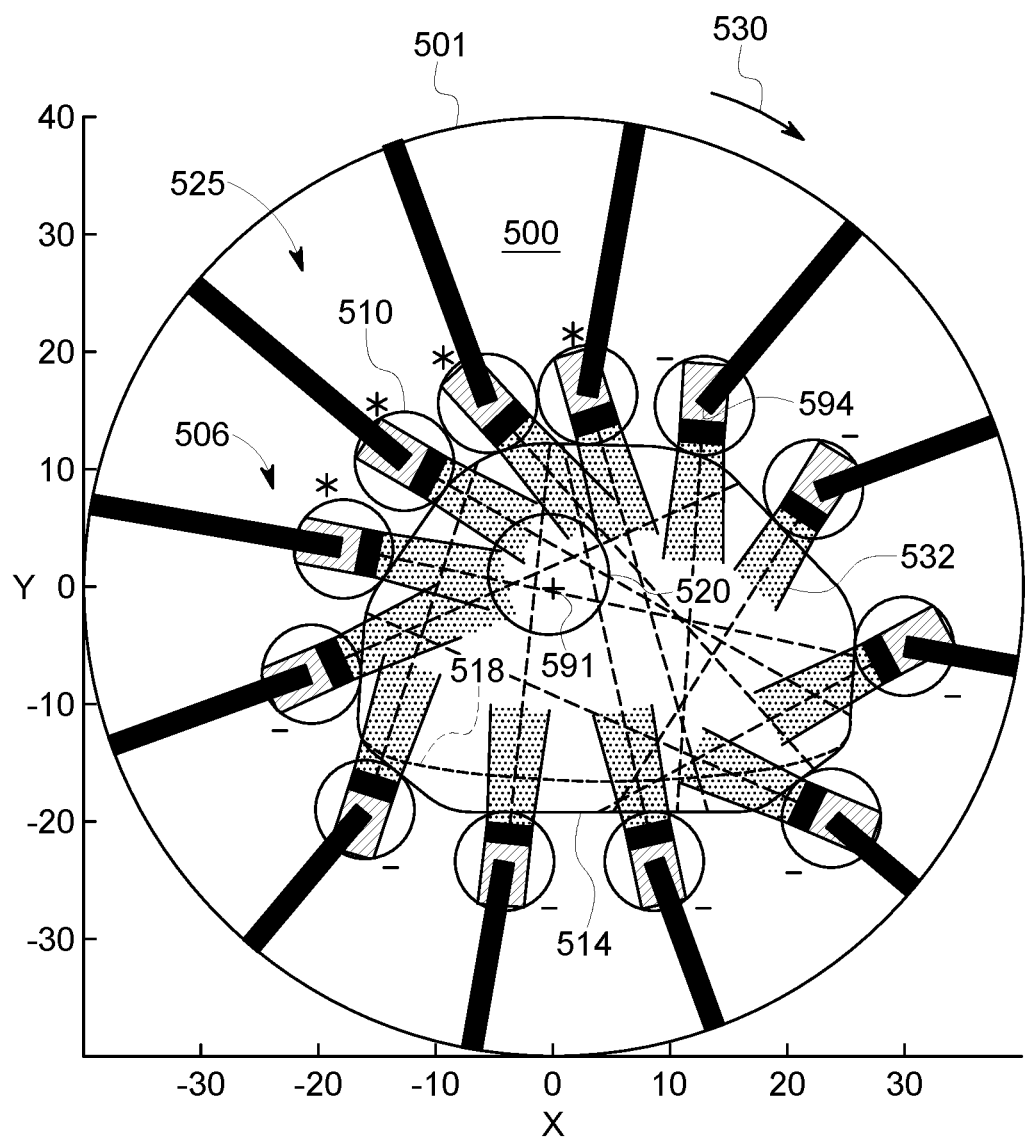
FIG. 14 is a schematic end view of the cavity of FIG. 10 illustrating an imaging session in which image data for diagnostic images is acquired.

FIG. 14 is a schematic end view of the cavity 500 during an imaging session in which the detector heads 510 are rotated about the respective sweep axes 594. As shown, the detector heads 510 are positioned such that a series of detector heads 510 are positioned in a dense group 525 that borders the body contour 514. The detector heads 510 may be immediately adjacent to the body contour 514 (or patient). In particular embodiments, the series of detector heads 510 includes the detector heads 510 from at least three adjacent detector assemblies 506. The detector heads 510 within the dense group 525 may be referred to as primary detector heads 510. The remaining detector heads 510 (or those not within the dense group 525) may be referred to as secondary detector heads 510. The primary detector heads 510 are identified with (*), and the secondary detector heads 510 are identified with (-). In FIG. 14, the dense group 525 includes four (4) primary detector heads.

The dense group of the primary detector heads may include at least one of (a) two or more of the primary detector heads being immediately adjacent to one another such that the primary detector heads abut each other or have a nominal or tolerance gap therebetween or (b) two or more of the primary detector heads are incapable of moving closer to the patient because the primary detector heads are extended to a maximum radial distance or blocked by another primary detector head.

Alternatively or in addition to the above, the detector heads in the array are spaced apart from adjacent detector heads by respective separation distances. As described below, the primary detector heads of the dense group may have an average separation distance between one another. The average separation distance between the primary detector heads may be less than an average separation distance between the other detector heads.

Also shown in FIG. 14, the array 504 (FIG. 10) of the detector assemblies 506 has been rotated, as a group, about the longitudinal axis 591 to have a designated rotational orientation. More specifically, the gantry 501 has been rotated (as indicated by the arrow 530) about the longitudinal axis 591, thereby moving the array 504 and the detector heads 510. The array 504 has a different rotational orientation in FIG. 14 compared to FIG. 13. The rotating of the gantry 501 may occur prior to moving the detector heads 510 and/or prior to moving the table 518 as described above. Alternatively or in addition to the above, the rotating of the gantry 501 may occur after moving the detector heads 510 and/or after moving the table 518. When the detector heads 510 and the body contour 514 have a designated spatial relationship, the imaging system may acquire image data. The image data may be used to diagnose a health status of the patient.

Each of the detector heads 510 has a respective field-of-view (FOV) 532. The FOV 532 represents the space from which emitted photons may be detected by the corresponding detector head 510. Each of the detector heads 510 has a designated rotational orientation relative to the sweep axis 594. As such, each of the FOVs 532 has the designated rotational orientation. In certain embodiments, the detector heads 510 acquire image data of the ROI 520 at a series of rotational orientations. For example, the detector heads 510 may acquire image data every 5° at four different rotational orientations. In other embodiments, the detector heads 510 acquire image data at only a single rotational orientation.

Figure 15:
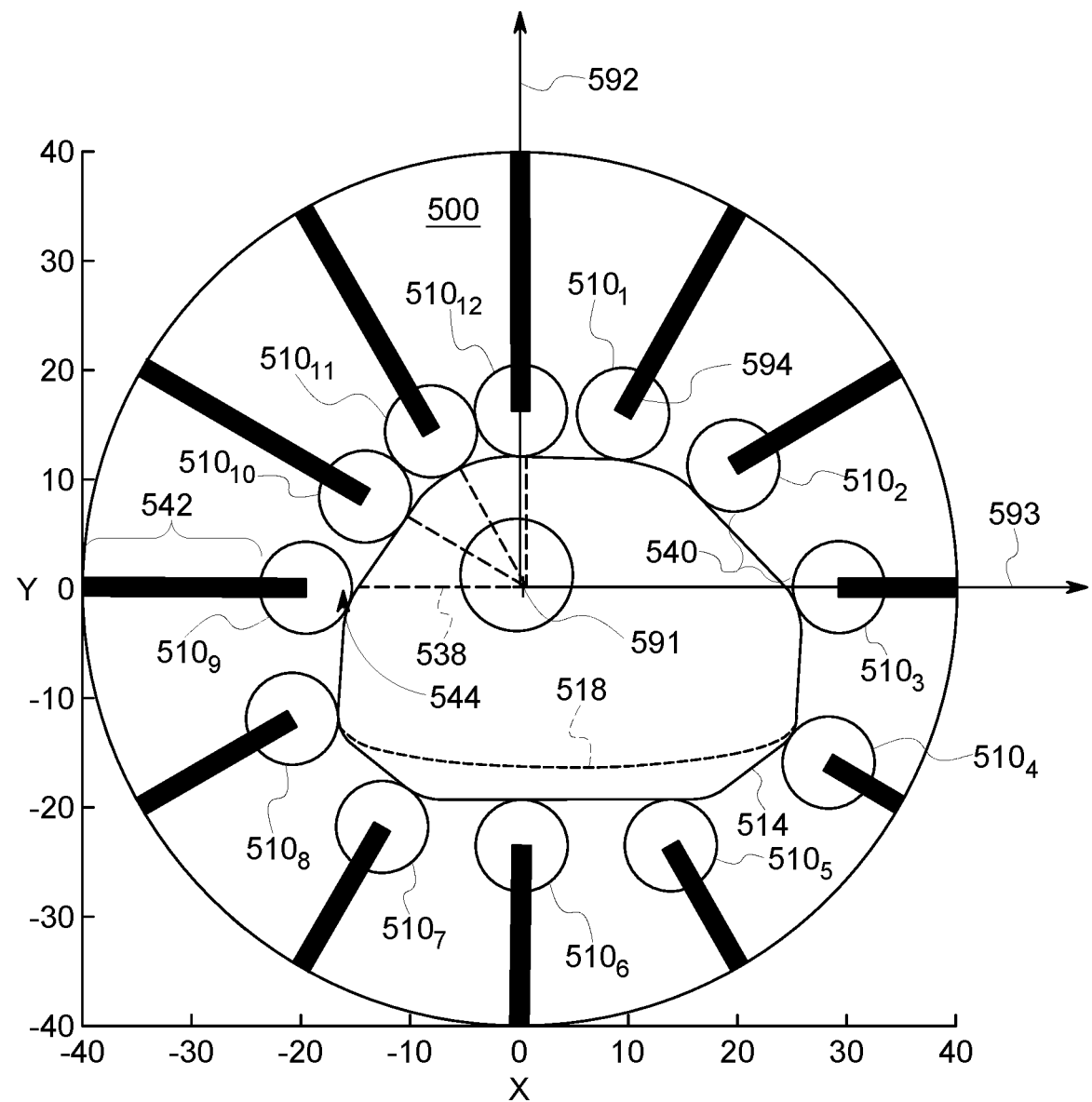
FIG. 15 is a schematic end view of the cavity of FIG. 10 illustrating different spatial relationships that may be determined for positioning the detector heads.

FIG. 15 is a schematic end view of the cavity 500 illustrating different spatial relationships that may be determined for positioning the detector heads 510 and/or the body contour 514. Embodiments are configured to determine a designated acquisition configuration that may acquire more photons compared to at least some other acquisition configurations. Each acquisition configuration may have (1) a designated position of the table 518 within the cavity 500; (2) a designated rotational orientation of the array 504 (FIG. 10) of the detector assemblies 506 (or the gantry 501); (3) a designated number of detector heads 510, which may include all of the detector heads in the array 504 or fewer detector heads; (4) designated radial positions of the detector heads 510 within the cavity; and/or (5) designated rotational orientations of the detector heads 510 about respective sweep axes 594. Based on the acquisition configuration, embodiments are configured to (a) rotate, as a group, the detector heads 510 about the longitudinal axis 591; (b) move the table 518 along at least one of the longitudinal axis 591, the vertical axis 592, or the lateral axis 593; (b) move at least one of the detector heads 510 in a radial manner toward or away from a center of the cavity or the patient; (c) rotate at least one of the detector heads 510 about the respective sweep axes 594.

To determine the acquisition configuration, embodiments may use body-contour information from the patient and a system matrix of the NM imaging system. Optionally, the determination may also be based on the designated protocol (e.g., cardiac or brain) and/or ROI information. A system matrix generally defines the mechanical capabilities of the NM imaging system for moving the different components. The system matrix may essentially be a mathematical description of the NM imaging system that may be used to determine what positions are possible for the different components for imaging the ROI. For example, the system matrix may include mechanical and physical characteristics of the gantry (e.g., size, range of rotational orientations, such 0°-540°), mechanical and physical characteristics of the movable arms (e.g., a minimum length when fully retracted, a maximum length when fully extended, speed at which the movable arms may operate), mechanical and physical characteristics of the detector heads (e.g., size of the detector head, range of rotational orientations, size of the FOV of the detector head, type of collimator used by the detector head), and mechanical and physical characteristics of the table (e.g., size of the table, a range of positions that the table may have, and a speed at which the table may be moved).

The body-contour information characterizes the body contour of the patient and, optionally, also the table. In some embodiments, the body contour information may be determined by the PSDs. For example, the PSDs may advance toward the patient when the patient is positioned within the cavity. When the PSDs engage the patient, the PSDs are activated and communicate signals indicating that the PSDs have contacted the patient. Based upon the position of the detector heads when the PSDs are activated, a body-contour may be determined.

Other methods for determining a body contour may be used. For example, as the patient is advanced into the cavity, the body of the patient may be scanned to determine a three-dimensional representation of the patient. As another example, a camera may be aligned with the cavity. As the detector heads approach the patient, the image data may be analyzed to determine when the detector heads are properly positioned.

The ROI information characterizes a location of the ROI within the patient (or body contour). The ROI information may be based on the designated protocol (e.g., cardiac protocol). For example, the NM imaging system may align the detector heads with a region where the ROI should be located. The ROI information may include image data. For example, persistence images may be acquired and the ROI may be determined based on the persistence images.

The acquisition configuration may be determined using one or more spatial relationships. For example, FIG. 15 shows detector heads 510$_1$-510$_{12}$ of the array 504 in which the detector heads are positioned similar to numbers on a clock. The acquisition configuration may be based on one or more distances that separate different elements and/or one or more distances that separate elements from reference points. For instance, a working distance 538 extends between each detector head 510 and the longitudinal axis 591. A separation distance 540 separates each detector head 510 from an adjacent detector head 510. Each of the detector heads 510 may be positioned a radial distance 542 away from a minimum radial position, such as the minimum radial positions shown in FIG. 11. Alternatively or in addition to the above, the acquisition configuration may be based on predicted photon-detection rates for the detector heads that are derived from persistence images.

The following describes different methods for determining an acquisition configuration. It should be understand that the examples may be modified and/or may calculate only one factor of other factors considered in determining the acquisition configuration. In many implementations, at least one of the detector heads will be immediately adjacent to the patient such that the detector head is engaging the patient or the detector head has a nominal gap (e.g., at most two centimeters). In some implementations, each and every primary detector head is positioned immediately adjacent to the patient.

In some embodiments, the acquisition configuration is based on or a function of the working distances 538 between the primary detector heads and a common reference point or axis. For example, the acquisition configuration may be based on an average working distance of the primary detector heads 510$_9$-510$_{12}$ of the dense group 525. The working distance 538 is measured between a common reference point of each detector head to a common spatial point or common axis. In FIG. 15, the working distance 538 for each detector head 510 extends between a front surface 544 of the detector head 510 and the longitudinal axis 591. The front surface 544 is the closest point of the detector head 510 to the longitudinal axis 591. For instance, if the detector heads 510 are pressed to the body, the body contour and the position of the detector head 510 within the cavity 500 may be assumed to be the same. For each possible position of the body contour, the working distances 538 may be calculated between the longitudinal axis 591 and the detector heads 510. An average working distance may be calculated for a plurality of possible acquisition configurations. For example, an average working distance may be calculated for a plurality of possible positions of the body contour. The average working distance is the sum of the working distances of the primary detector heads for one possible position of the body contour divided by the total number of primary detector heads. The positions of the primary detector heads for the acquisition configuration may be the positions that the primary detector heads have when a minimum value of the average working distances occurs. In other words, the selected acquisition configuration may include the position of the body contour and the positions of the primary detector heads when a minimum average working distance occurs.

In calculating the working distances and the average working distance or in selecting the acquisition configuration, one or more rules may be followed. For example, the detector heads may not exceed a designated maximum or minimum radial position and/or may not be positioned where the detector heads might physically damage each other. As an example of another rule, it may be required that two of the detector heads be separated by at least a designated distance or that the detector heads have designated positions with respect to the ROI. For instance, a rule may require that the detector head $510_{12}$ and the detector head $510_9$ acquire a top view and a side view, respectively, of the ROI. As another example, a rule may limit the possible acquisition configurations. For instance, a rule may restrict the table motion to vertical motion alone.

In some embodiments, the acquisition configuration is based on or a function of the separation distances 540 between the primary detector heads. For example, the detector heads $510_1$-$510_{12}$ are pressed to the body and spaced apart from adjacent detector heads by respective separation distances 540. Two detector heads are adjacent if no other detector head is positioned between the two detector heads. In some cases, adjacent detector heads are at risk of engaging each other if permitted to extend further radially inward. By way of example, in FIG. 15, the detector head $510_{12}$ is adjacent to detector head $510_1$ and adjacent to detector head $510_{11}$. The detector head $510_1$ and the detector head $510_{11}$ are not adjacent to each other because the detector head $510_{12}$ is positioned between detector heads $510_1$, $510_{11}$.

The primary detector heads $510_9$-$510_{12}$ of the dense group 525 have an average separation distance between one another. The average separation distance is the sum of the separation distances 540 between the primary detector heads $510_9$-$510_{12}$. The positions of the primary detector heads $510_9$-$510_{12}$ for the acquisition configuration may be the positions that the primary detector heads $510_9$-$510_{12}$ have when a minimum value of the average separation distances occurs. In other words, the acquisition configuration may be the position of the body contour and the positions of the primary detector heads when the primary detector heads $510_9$-$510_{12}$ have the tightest or most packed configuration. Generally, the average separation distance between the primary detector heads $510_9$-$510_{12}$ is less than an average separation distance between the other detector heads in the acquisition configuration.

In some embodiments, the acquisition configuration is based on or a function of the radial distances 542 of the primary detector heads $510_9$-$510_{12}$. As described herein, the detector heads 510 are configured to move within a radial range defined between a minimum radial distance and a maximum radial distance. The maximum radial distance may be a point at which the primary detector head cannot move closer to the object (e.g., point at which the primary detector head engages the object). For example, at least one of the primary detector heads may not be able to move closer to the object because of another detector head or because the movable arm may be fully extended. In some instances, the positions of the primary detector heads $510_9$-$510_{12}$ for the acquisition configuration may be the positions that the primary detector heads $510_9$-$510_{12}$ have when a maximum of an average of the radial distances of the primary detector heads $510_9$-$510_{12}$ occurs. In such instances, at least one of the primary detector heads is typically positioned immediately adjacent to the patient (e.g., engaged to the patient).

In some embodiments, the acquisition configuration is based on or a function of the photon-detection rates of the primary detector heads $510_9$-$510_{12}$. After acquiring persistence images, the persistence image data may be analyzed to predict where a maximum photon-detection rate (or at least a threshold photon-detection rate) will occur for each of the detector heads. Accordingly, embodiments may be configured to determine positions of the primary detector heads at which a more desirable photon-detection rate is expected.

The acquisition configuration may be a function of one or more factors. For example, an algorithm may determine the acquisition configuration by (a) identifying a plurality of positions of the primary detector heads in which the average radial distance is at least X; (b) identifying a plurality of positions of the primary detector heads in which the average working distance is at most Y; (c) identifying a plurality of positions of the primary detector heads in which the average separation distance is at most Z. For the possible positions that satisfy (a), (b), and (c), the acquisition configuration may be determined by identifying (e.g., through calculating or predicting) where at least a threshold photon-detection rate will occur for the possible positions. After selecting the acquisition configuration, the table and/or the gantry may be moved automatically by the system or manually by a technician. The detector heads are typically moved automatically by the system.

Figure 16:
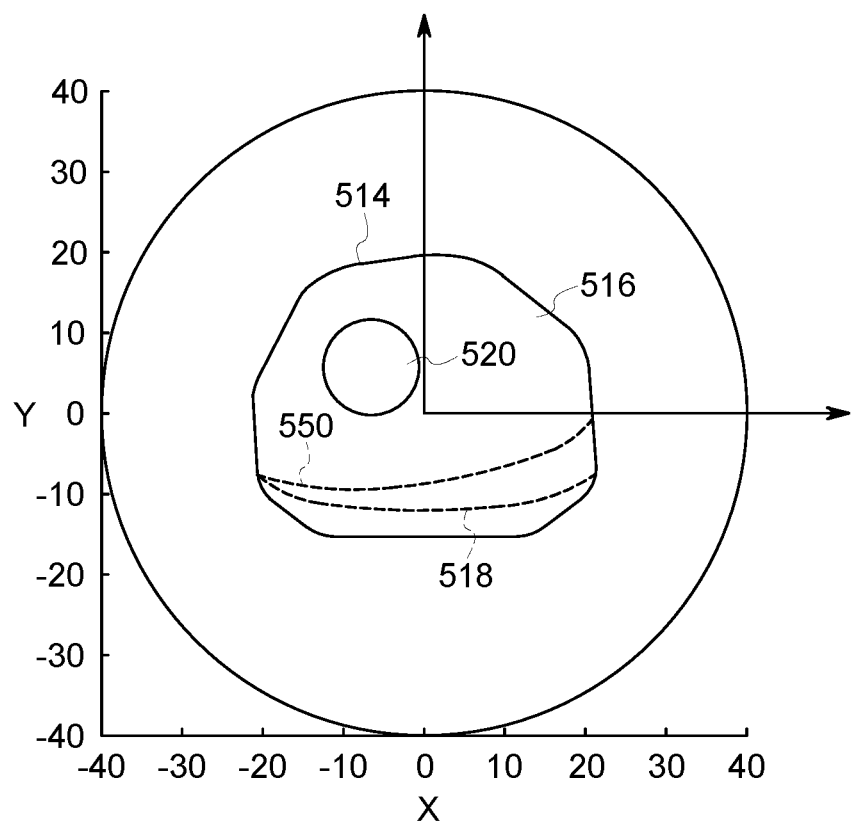
FIG. 16 is a schematic end view of the cavity of FIG. 10 illustrating a local support that may be positioned to change an orientation of the object.

FIG. 16 is a schematic end view of the cavity of FIG. 10 illustrating a local support 550 that may be positioned to change an orientation of the patient. As shown, the body contour 514 includes the patient 516, the table 518, and a local support 550. For some embodiments, a local support 550 may be positioned between the patient 516 and the table 518 to adjust an orientation of the patient or to change the body contour 514. The local support 550 may be positioned, for example, between a torso of the patient 516 and a top surface of the table 518. The patient 516 may rest upon the local support 550 as the patient 516 moves into the cavity 500. For such embodiments, the system may determine a body contour 514 of the patient with the local support 550 positioned between the patient 516 and the table 518.

Optionally, embodiments may determine that a better acquisition configuration may be achieved if the patient 516 rests upon the local support 550. In such instances, a body contour of the patient 516 is determined. Persistence images may be acquired to estimate a location of the ROI 520. Based upon an analysis of the ROI 520 and the body contour 514, the system (e.g., at least one processor) may determine that an orientation of the body contour 514 can be changed to enable detecting more photons emitted from the ROI 520 and/or enable imaging the ROI 520 at a different orientation.

Figure 17:
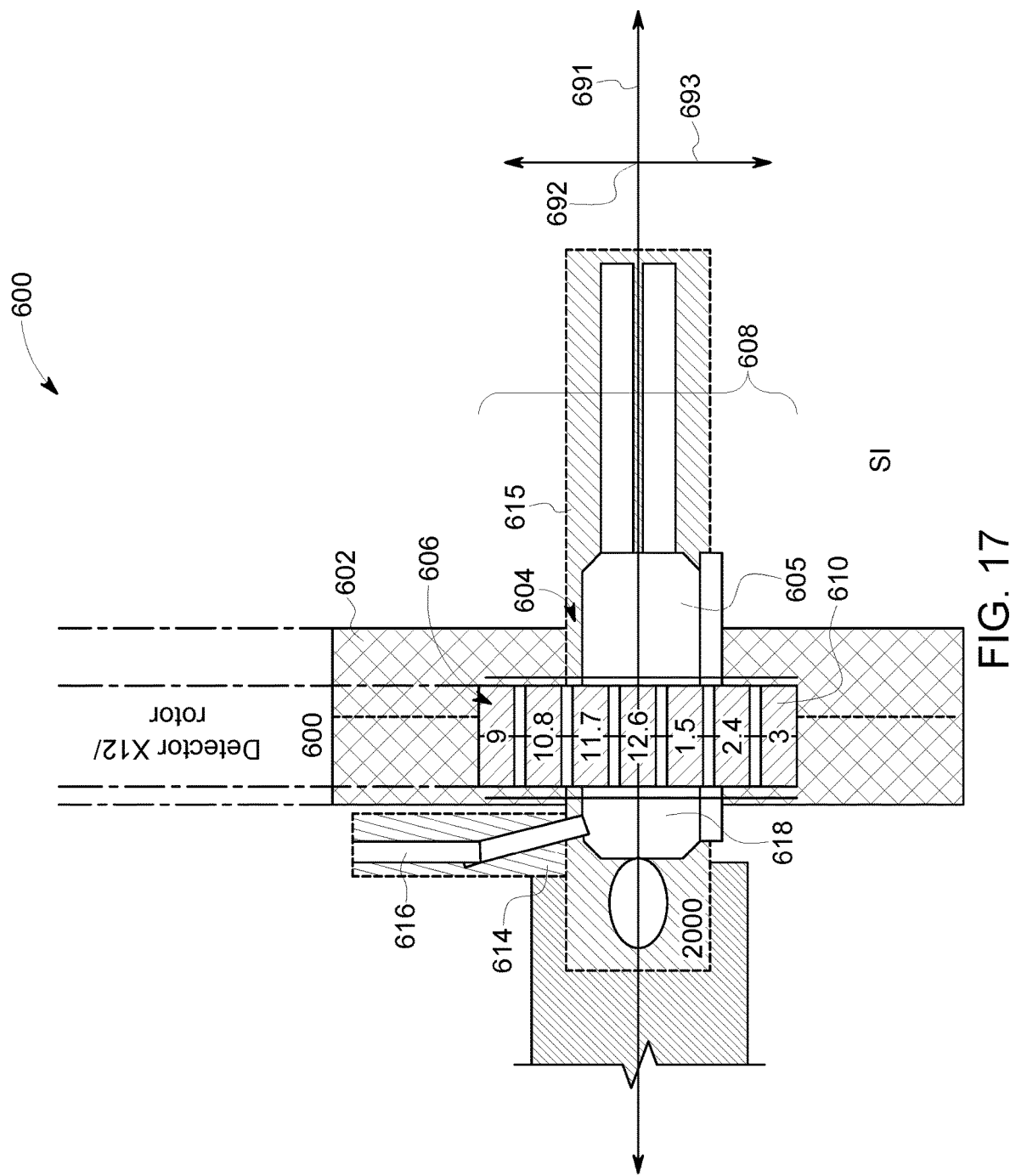
FIG. 17 is a schematic view of an imaging system in which a local support is used to support an arm of a patient outside of the cavity.

FIG. 17 is a schematic view of an NM imaging system 600 in accordance with an embodiment. The NM imaging system 600 may include elements that are similar or identical to the elements of the NM imaging systems 100 (FIG. 1), 181 (FIG. 2) and be capable of determining an acquisition configuration as described herein. For example, the NM imaging system 600 has a gantry 602 including a cavity 604 that is sized and shaped to receive a patient 605 therein. The cavity 604 is oriented relative to mutually perpendicular longitudinal, vertical, and horizontal axes 691, 692, 693. The cavity 604 extends lengthwise along the longitudinal axis 691. The gantry 602 has a discrete housing and is configured to rotate at a rotational speed in one or both directions about the longitudinal axis 691.

The NM imaging system 600 also includes a plurality of detector assemblies 606. The detector assemblies 606 are positioned in an array 608 in which the detector assemblies 606 are distributed at least partially around the cavity 604. In the illustrated embodiment, the detector assemblies 606 are evenly distributed circumferentially about the longitudinal axis 691. Each of the detector assemblies 606 includes a movable arm (not shown) and a detector head 610 that is coupled to the movable arm. The movable arm is configured to move the detector head 610 toward and away from the object within the cavity 604.

The NM imaging system 600 also includes a movable table 615. The movable table 615 is configured to receive the patient and move the patient into the cavity 604. In some embodiments, the movable table 615 may move in one or both directions along the vertical axis 692 and in one or both directions along the horizontal axis 693. Movement along the vertical axis 692 and the horizontal axis 693 may occur simultaneously or in separate movements (e.g., first up, then over). As set forth herein, the NM imaging system 600 may move the detector heads 610 and the movable table 615 so that a series of detector heads 610 are positioned in a dense group that borders the object.

In some embodiments, the NM imaging system 600 may include a local support 614. The local support 614 is an extremity or local support in FIG. 17. The local support 614 is used to support an arm 616 of a patient outside of the cavity 604. In some embodiments, one or more protocols may be configured to image the ROI without the arm 616 of the patient be positioned alongside the torso 618 of the patient. As shown, the local support 614 may be positioned proximate to the patient such that the arm 616 of the patient may rest upon the local support 614 during imaging. In such instances, the detector heads 610 may be positioned closer to the torso 618 of the patient. Similar to the local support 550 (FIG. 16), embodiments may determine that a better acquisition configuration may be achieved if the arm 616 of the patient is removed from the body contour. In such instances, the local support 616 may be added after the patient is initially scanned for determining a body contour.

Figure 18:
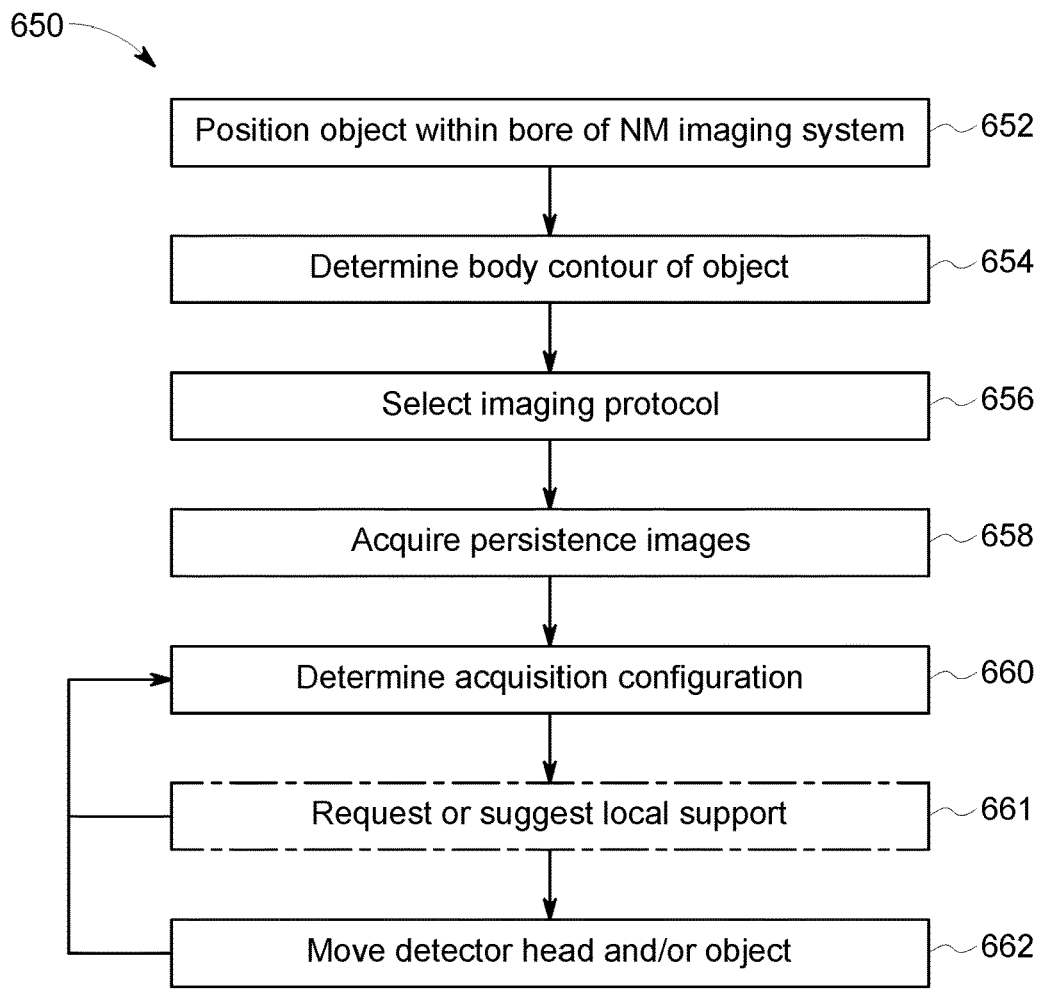
FIG. 18 is a flowchart illustrating a method in accordance with an embodiment.

FIG. 18 is a flowchart illustrating a method 650 in accordance with an embodiment. The method 650 may be carried out or performed using an NM imaging system, such as the NM imaging systems set forth herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

At 652, an object is positioned within a cavity of the NM imaging system. In particular embodiments, the object is a patient (e.g., human or animal), but other objects may be imaged. The cavity is sized and shaped to receive the object therein. An array of detector assemblies are distributed at least partially around the cavity. Each of the detector assemblies in the array includes a movable arm and a detector head that is coupled to the movable arm.

Positioning the object, at 652, may include positioning the object on a movable table and moving the table into the cavity. One or more motors operably connected to the table may move the object longitudinally into the cavity, horizontally, or vertically. In other embodiments, a chair or other patient support device may hold the patient at a designated position. The gantry may be lowered or otherwise moved such that the patient is positioned within the cavity.

At 654, a body contour of the object within the cavity is determined. The body contour represents an exterior surface of the object positioned within the cavity. The body contour may be determined by at least one processor. For example, the object may be scanned along a plane that is transverse to the longitudinal axis as the object is moved into the cavity. As described above, LEDs and light sensors may be used to determine a two-dimensional or three-dimensional contour of the object. Alternatively or in addition to the above, the body contour may be determined using PSDs and/or cameras. Data may be communicated to the at least one processor to determine the body contour. The body contour includes the object. Optionally, the body contour also includes the table supporting the object.

As another example, the body contour may be determined from image data that is acquired using depth cameras and optional projectors. Such image data may be used to model three-dimensional surface geometry.

At 656, an imaging protocol is selected. For example, an operator or technician may select a type of imaging protocol, such as a brain protocol, cardiac protocol, or one or more extremity protocols. The type of protocol may identify the region-of-interest (e.g., organ-of-interest). After receiving user inputs that identify the type of protocol, the system may determine an acquisition configuration for the imaging protocol. More specifically, the system may determine relative positions of the detector heads and the table. A system may automatically determine the acquisition configuration based on the region-of-interest (e.g., brain, heart, etc.) and the body contour determined at 654.

In some embodiments, the system may utilize anatomical atlases for estimating a location of the ROI within the body. With this estimated location and the known body contour, the system may automatically select the relative positions of the detector heads and the table.

Alternatively or in addition to using an anatomical atlas, the system may analyze persistence images. In such optional embodiments, the persistence images may be acquired at 658. The persistence images may have a lower quality than the diagnostic images. For example, the time period for detecting the photons during persistence imaging is shorter than the time period for detecting the photons during diagnostic imaging. Embodiments may search for the ROI within the persistence images that is approximately located within a larger region identified using the anatomical atlases. For example, embodiments may first identify a larger region that will include the ROI using an anatomical atlas. Embodiments may then analyze the larger region within the persistence images to determine the ROI. As one particular example, if the protocol is a cardiac protocol, the system may use an anatomical atlas to identify an upper portion of the torso and then use persistence images to determine where the ROI is located within the upper portion of the torso. Alternatively, embodiments may use only the persistence images to identify the location of the ROI. Alternatively, the ROI may be determined manually or by analyzing data from another imaging modality such as CT.

At 660, an acquisition configuration may be determined. The acquisition configuration may identify the detector heads that will provide the most high quality image data (e.g., detect the most photons). These detector heads may be referred to as the primary detector heads. For example, three primary detector heads may be positioned to surround at least a part of the ROI (60°). The acquisition configuration may also identify a position of the body contour (or position of the table) and positions of the detector heads. The positions of the detector heads may also include an orientation and sweep range for the detector head.

To determine the acquisition configuration, at least one processor may use a body-contour of the object and a system matrix of the NM imaging system. Optionally, the determination may also be based on the designated protocol (e.g., cardiac or brain) and/or a location of the ROI. The acquisition configuration may be based on one or more spatial parameters. For example, an algorithm may determine the acquisition configuration based on at least one of: (a) a minimum average working distance of at least two of the primary detector heads in which the working distance is measured from the detector head to a designated point (e.g., longitudinal axis); (b) a maximum average radial distance in which at least two of the primary detector heads have been extended; and (c) a minimum of an average separation distance between at least two of the primary detector heads. The acquisition configuration may also be determined by identifying where a more desirable photon-detection rate (e.g., maximum photon-detection rate) will occur for the primary detector heads.

At 662, at least one of the detector heads or the body contour is moved so that the detector heads and the body contour have the acquisition configuration. In some embodiments, the body contour is moved away from the primary detector heads. For instance, if the primary detector heads are detector heads $510_{11}$, $510_{12}$, $510_1$, then the body contour is moved generally toward the detector heads $510_5$, $510_6$, $510_7$. If the primary detector heads are detector heads $510_9$, $510_{10}$, $510_{11}$, and $510_{12}$, then the body contour is moved generally toward the detector heads $510_3$, $510_4$, $510_5$, and $510_6$.

In some embodiments, after moving the detector heads and/or the body contour, the method may determine another acquisition configuration. For example, the detector heads may engage the object within the cavity as the detector heads move to the designated positions of the acquisition configuration. If the detector heads include PSDs, the PSDs may communicate information to the system for confirming or re-calculating the acquisition configuration. In some embodiments, the determining at 660 and moving at 662 occurs iteratively until a desired or improved acquisition configuration is achieved.

In some embodiments, more than one acquisition configuration may be used. For example, a first acquisition configuration may be used to acquire image data using a plurality of primary detector heads. Subsequently, a second acquisition configuration may be used to acquire image data using a plurality of primary detector heads. The first and second acquisition configurations may have different positions for the table and use at least one different primary detector head.

In some embodiments, the acquisition configuration forms a series of primary detector heads that are positioned in a dense group. The primary detector heads may border the body contour. For example, the primary detector heads may engage the object or have a nominal gap therebetween. In particular embodiments, the primary detector heads include at least three detector heads that are from adjacent detector assemblies.

Optionally, at 661, a local support may be requested or suggested. The local support may be used to change an orientation and/or size of the body contour. For example, each of the local supports may have a known size and shape. While determining the acquisition configuration at 660, the system may determine that the body contour should have a different orientation and/or size. The system may request or suggest the local support (e.g., arm support or torso support) by generating a visual or audio notification.

For example, the system may determine that the primary detector heads will have better imaging positions if a designated local support is used to change an orientation and/or size of the portion of the body contour that is bordered by the dense group of primary detector heads. To determine whether the primary detector heads will have better imaging positions, the system may calculate one or more of the parameters, such as those described above, assuming that a local support is used. For example, the system may determine, while assuming a designated local support is used, the working distances of the respective primary detector heads, the radial distances of the respective primary detector heads, and/or the separation distances between adjacent primary detector heads. The system may determine that a designated local support should be used if, for example, the minimum of the average working distance, the maximum of the average radial distance, and/or the minimum of the average separation distance occurs using the local support. As described above, each of these parameters may be used exclusively to determine the acquisition configuration or may be one of a plurality of parameters considered in determining the acquisition configuration.

Figure 22:
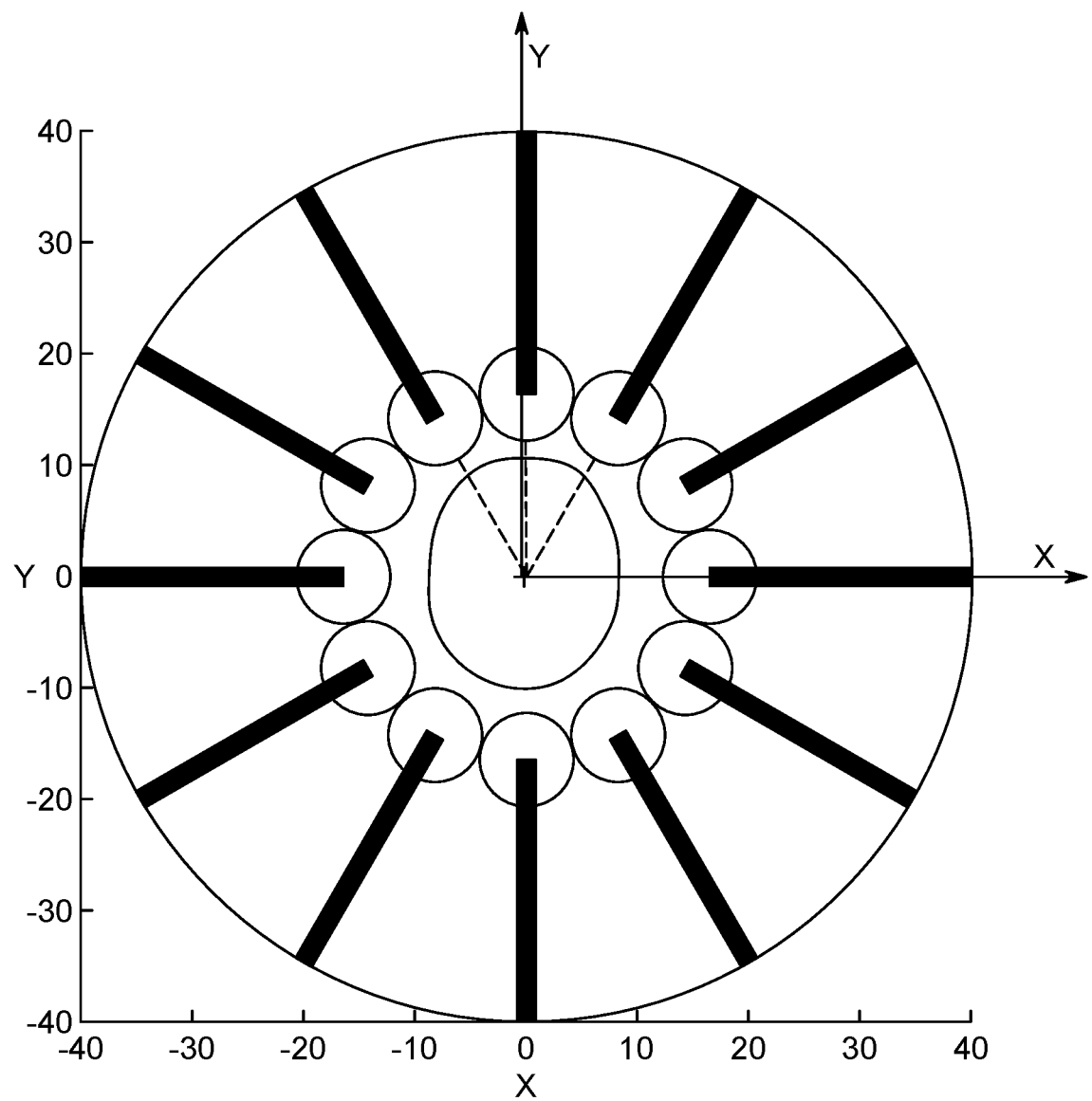
FIG. 22 is a schematic end view of a cavity having an array of detector assemblies positioned therein in accordance with an embodiment for imaging a head.
Figure 23:
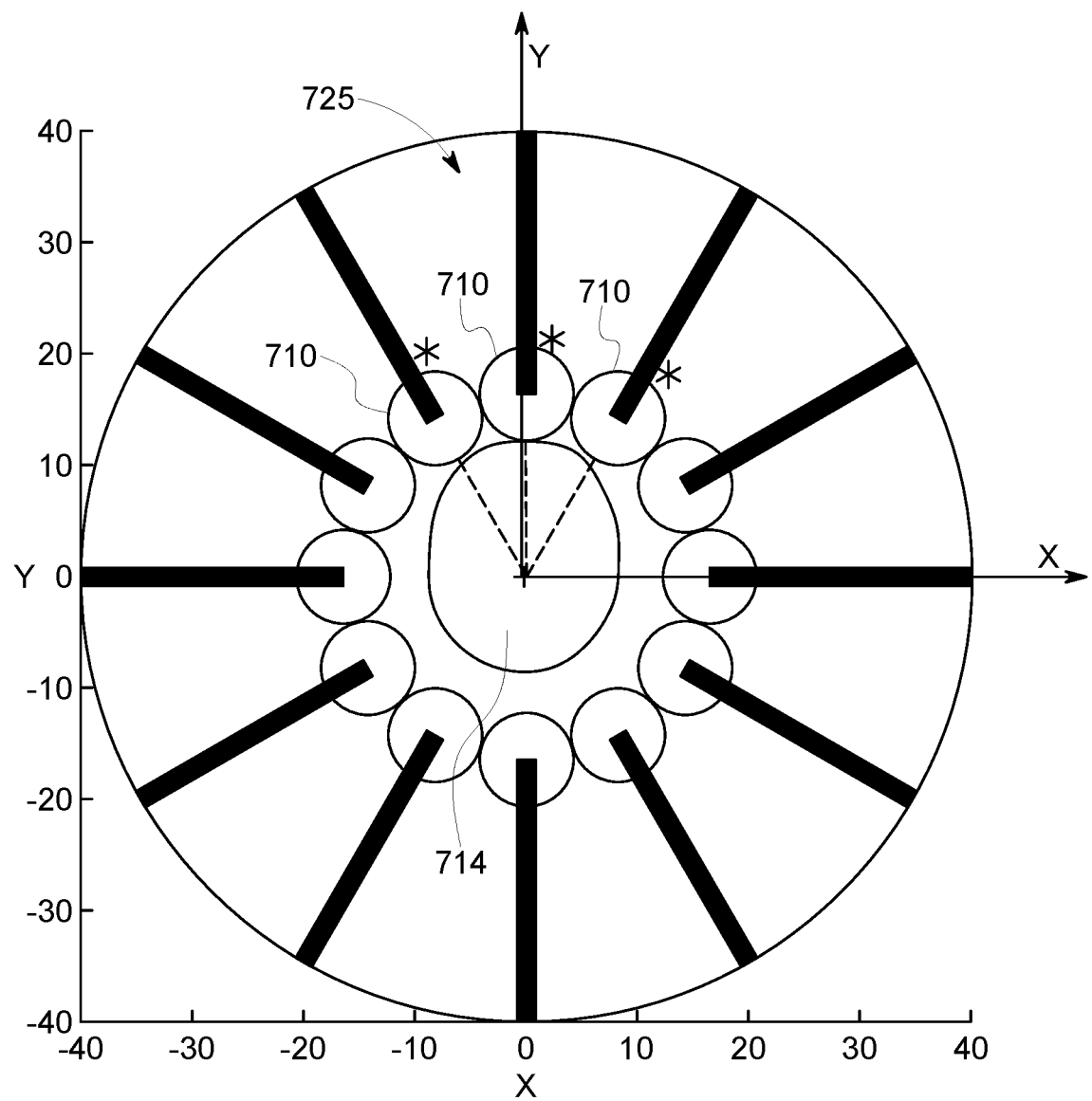
FIG. 23 is a schematic end view of the cavity of FIG. 22 illustrating a position of the head after moving the patient.

FIGS. 22 and 23 illustrate an implementation in which a patient 714 is moved toward primary detector heads 710 so that a dense group 725 of detector heads may border the patient. In FIGS. 22 and 23, each of the detector heads 710 is at the maximum radial position such that the detector heads 710 may not be moved closer to the patient 714. Nonetheless, gaps exist between the detector heads 710 and the patient 714. This may occur when, for example, the portion of the patient to be imaged is a head or an extremity or the patient is a child. In such circumstances, embodiments may determine that the patient 714 should be moved toward the primary detector heads 710. Relative to FIG. 23, the patient 714 has been moved vertically toward the primary detector heads 710.

As used herein, a processor or a processing unit includes processing circuitry configured to perform one or more tasks, functions, or steps, such as those described herein. For instance, the processor may be a logic-based device that performs operations based on instructions stored on a tangible and non-transitory computer readable medium, such as memory. It may be noted that a "processor," as used herein, is not intended to necessarily be limited to a single processor or single logic-based device. For example, the processor may include a single processor (e.g., having one or more cores), multiple discrete processors, one or more application specific integrated circuits (ASICs), and/or one or more field programmable gate arrays (FPGAs). In some embodiments, the processor is an off-the-shelf device that is appropriately programmed or instructed to perform operations, such as the algorithms described herein.

The processor may also be a hard-wired device (e.g., electronic circuitry) that performs the operations based on hard-wired logic that is configured to perform the algorithms described herein. Accordingly, the processor may include one or more ASICs and/or FPGAs. Alternatively or in addition to the above, the processor may include or may be associated with a tangible and non-transitory memory having stored thereon instructions configured to direct the processor to perform the algorithms described herein.

It is noted that operations performed by the processor (e.g., operations corresponding to the methods/algorithms described herein, or aspects thereof) may be sufficiently complex that the operations may not be performed by a human being within a reasonable time period based on the intended application of the assay system. The processor may be configured to receive signals from the various subsystems and devices of the system or user inputs from the user. The processor may be configured to perform the methods described herein.

Processors may include or be communicatively coupled to memory. In some embodiments, the memory may include non-volatile memory. For example, the memory may be or include read-only memory (ROM), random-access memory (RAM), electrically erasable programmable read-only memory (EEPROM), flash memory, and the like. The memory may be configured to store data regarding operating parameters of the system.

In an exemplary embodiment, the processor executes a set of instructions that are stored in one or more storage elements, memories, and the like. Embodiments include non-transitory computer-readable media that include set of instructions for performing or executing one or more processes set forth herein. Non-transitory computer readable media may include all computer-readable media, except for transitory propagating signals per se. The non-transitory computer readable media may include generally any tangible computer-readable medium including, for example, persistent memory such as magnetic and/or optical disks, ROM, and PROM and volatile memory such as RAM. The computer-readable medium may store instructions for execution by one or more processors.

The set of instructions may include various commands that instruct the system to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A nuclear medicine (NM) imaging system comprising:
a gantry including a cavity that is sized and shaped to receive an object therein, the cavity being oriented relative to mutually perpendicular longitudinal, vertical, and horizontal axes, the cavity extending lengthwise along the longitudinal axis;
a plurality of detector assemblies distributed at least partially around the cavity, each of the detector assemblies in the plurality including a movable arm and a detector head that is coupled to the movable arm, the movable arm configured to move the detector head toward and away from the object within the cavity;
a table positioned within the cavity and extending lengthwise along the longitudinal axis, the table configured to support the object; and
at least one processor configured to execute programmed instructions stored in memory, wherein the at least one processor, when executing the programmed instructions, is configured to:
determine a body contour of the object within the cavity, the body contour representing an exterior surface of the object positioned within the cavity;
determine an acquisition configuration based on the body contour, the acquisition configuration including at least three of the detector heads as primary detector heads that acquire image data of the object for diagnostic images, the acquisition configuration configured to reduce gaps between the primary detector heads and position the primary detector heads along the body contour; and
direct the table to move at least partially along the horizontal axis and direct the respective detector assemblies to move at least two of the primary detector heads so that the primary detector heads are positioned in accordance with the acquisition configuration that reduces the gaps.

2. The NM imaging system of claim 1, wherein the at least one processor is instructed to reduce the gaps between the primary detector heads when determining the acquisition configuration, wherein at least one of the following exists after moving the at least two primary detector heads:
(a) two or more of the primary detector heads are immediately adjacent to one another such that the primary detector heads abut each other or have a tolerance gap therebetween of at most two centimeters; or
(b) two or more of the primary detector heads are incapable of moving closer to the object because the primary detector heads are extended to a maximum length or blocked by another primary detector head.

3. The NM imaging system of claim 1, wherein the primary detector heads have an average separation distance between one another, the average separation distance between the primary detector heads being less than an average separation distance between the other detector heads after the at least two primary detector heads are moved.

4. The NM imaging system of claim 1, wherein the longitudinal axis is a central longitudinal axis of the cavity and wherein each of the primary detector heads is positioned a working distance away from the longitudinal axis, the at least one processor configured to determine imaging positions of the primary detector heads by calculating a minimum of an average of the working distances of the primary detector heads, the acquisition configuration being at least partially based on positions of the primary detector heads where the minimum occurs.

5. The NM imaging system of claim 1, wherein the detector heads are configured to move within a radial range defined between a minimum radial distance and a maximum radial distance, the maximum radial distance being a point at which the primary detector head cannot move closer to the object, the at least one processor configured to determine imaging positions of the primary detector heads by calculating a maximum of an average of the radial distances of the primary detector heads, the acquisition configuration being at least partially based on positions of the primary detector heads where the maximum occurs.

6. The NM imaging system of claim 1, wherein the at least one processor is configured to determine imaging positions of the primary detector heads by calculating a minimum of an average separation distance between the primary detector heads, the acquisition configuration being at least partially based on positions of the primary detector heads where the minimum occurs.

7. The NM imaging system of claim 1, wherein the detector heads include photon detectors that are rotatable about a sweep axis, the at least one processor configured to acquire persistence images by detecting photons at different rotational positions of the photon detectors, the at least one processor also configured to determine imaging positions of the primary detector heads at which at least a threshold photon-detection rate is expected based on the persistence images, the acquisition configuration being at least partially based on the imaging positions at which a designated photon-detection rate is expected.

8. The NM imaging system of claim 1, wherein the at least one processor is configured to determine imaging positions of the primary detector heads for the acquisition configuration, wherein the imaging positions of the primary detector heads are a function of at least one of:
(i) an average working distance of the primary detector heads from the longitudinal axis, the longitudinal axis being a central longitudinal axis of the cavity;
(ii) an average radial distance of the primary detector heads from respective starting positions;
(iii) an average separation distance between the primary detector heads; or
(iv) a photon-detection rate based on persistence images acquired as the detector heads of the plurality of the plurality of detector assemblies rotated about a sweep axis.

9. A method comprising:
positioning an object within a cavity of a nuclear medicine (NM) imaging system, the NM imaging system including:
a cavity that is sized and shaped to receive an object therein, the cavity being oriented relative to mutually perpendicular longitudinal, vertical, and horizontal axes, the cavity extending lengthwise along the longitudinal axis;
a table positioned within the cavity and extending lengthwise along the longitudinal axis, the table configured to support the object; and
a plurality of detector assemblies distributed at least partially around the cavity, each of the detector assemblies in the plurality including a movable arm and a detector head that is coupled to the movable arm;

determining a body contour of the object within the cavity, the body contour representing an exterior surface of the object positioned within the cavity;

determining an acquisition configuration based on the body contour, the acquisition configuration including at least three of the detector heads as primary detector heads that are configured to acquire image data of the object for diagnostic images, the acquisition configuration configured to reduce gaps between the primary detector heads and position the primary detector heads along the body contour; and moving the table at least partially along the horizontal axis and moving at least two of the primary detector heads so that the primary detector heads are positioned in accordance with the acquisition configuration that reduces the gaps.

10. The method of claim 9, wherein at least one of the following exists after moving the at least two primary detector heads:

(a) two or more of the primary detector heads being immediately adjacent to one another such that the primary detector heads abut each other or have a tolerance gap therebetween; or (b) two or more of the primary detector heads being incapable of moving closer to the object because the primary detector heads are extended to a maximum length or blocked by another primary detector head.

11. The method of claim 9, wherein the primary detector heads have an average separation distance between one another, the average separation distance between the primary detector heads being less than an average separation distance between the other detector heads.

12. The method of claim 9, further comprising determining imaging positions of the primary detector heads, wherein the imaging positions of the primary detector heads are a function of at least one of:

(i) an average working distance of the primary detector heads from the longitudinal axis, the longitudinal axis being a central longitudinal axis of the cavity;

(ii) an average radial distance of the primary detector heads from respective starting positions; or (iii) an average separation distance between the primary detector heads.

13. The method of claim 9, further comprising determining imaging positions of the primary detector heads for the acquisition configuration, wherein the imaging positions of the primary detector heads are a function of at least one of:

(i) an average working distance of the primary detector heads from the longitudinal axis, the longitudinal axis being a central longitudinal axis of the cavity;

(ii) an average radial distance of the primary detector heads from respective starting positions;

(iii) an average separation distance between the primary detector heads; or (iv) a photon-detection rate based on persistence images acquired as the detector heads of the plurality of the plurality of detector assemblies rotated about a sweep axis.

14. A nuclear medicine (NM) imaging system comprising:

a gantry including a cavity that is sized and shaped to receive an object therein, the cavity being oriented relative to mutually perpendicular longitudinal, vertical, and horizontal axes, the cavity extending lengthwise along the longitudinal axis;

a table positioned within the cavity and extending lengthwise along the longitudinal axis;

a plurality of detector assemblies distributed at least partially around the cavity, each of the detector assemblies in the plurality including a movable arm and a detector head that is coupled to the movable arm, the movable arm configured to move the detector head toward and away from the object within the cavity; and at least one processor configured to execute programmed instructions stored in memory, wherein the at least one processor, when executing the programmed instructions, is configured to:

determine a body contour of the object within the cavity, the body contour representing an exterior surface of the object positioned within the cavity;

determine an acquisition configuration based on the body contour, the detector heads including at least three primary detector heads that are configured to acquire image data for diagnostic images, the acquisition configuration including the primary detector heads positioned to border the body contour; and direct, based on the acquisition configuration, the table to move the object away from one or more of the primary detector heads and direct the respective detector assemblies of at least two the primary detector heads to move the at least two primary detector heads toward the object.

15. The NM imaging system of claim 14, wherein the at least one processor, when executing the programmed instructions, is configured to direct the table to move the object at least partially along the horizontal axis away from the one or more primary detector heads.

16. The NM imaging system of claim 14, wherein at least one of the following conditions exists after moving the at least two primary detector heads:

(a) two or more of the primary detector heads being immediately adjacent to one another such that the primary detector heads abut each other or have a tolerance gap therebetween; or (b) two or more of the primary detector heads being incapable of moving closer to the object because the primary detector heads are extended to a maximum length or blocked by another primary detector head.

17. The NM imaging system of claim 14, wherein the primary detector heads have an average separation distance between one another, the average separation distance between the primary detector heads being less than an average separation distance between the other detector heads.

18. The NM imaging system of claim 14, further comprising determining imaging positions of the primary detector heads, wherein the imaging positions of the primary detector heads are a function of at least one of:

(i) an average working distance of the primary detector heads from the longitudinal axis, the longitudinal axis being a central longitudinal axis of the cavity;

(ii) an average radial distance of the primary detector heads from respective starting positions; or (iii) an average separation distance between the primary detector heads.

19. A method comprising:

positioning a patient within a cavity of a nuclear medicine (NM) imaging system, the NM imaging system including:

a cavity that is sized and shaped to receive the patient therein, the cavity being oriented relative to mutually perpendicular longitudinal, vertical, and horizontal axes, the cavity extending lengthwise along the longitudinal axis;

a table positioned within the cavity and extending lengthwise along the longitudinal axis, the table configured to support the patient;

a plurality of detector assemblies distributed at least partially around the cavity, each of the detector assemblies in the plurality including a movable arm and a detector head that is coupled to the movable arm;

determining a body contour of the object within the cavity, the body contour representing an exterior surface of the object positioned within the cavity;

determining an acquisition configuration based on the body contour, the detector heads including at least three primary detector heads that are configured to acquire image data for diagnostic images, the acquisition configuration including the primary detector heads positioned to border the body contour; and directing, based on the acquisition configuration, the table to move the object away from one or more of the primary detector heads and directing, based on the acquisition configuration, the respective detector assemblies of at least two the primary detector heads to move the at least two primary detector heads toward the object.

20. The method of claim 19, further comprising moving the table at least partially along the horizontal axis.

* * * * *